United States Patent
O'Rourke et al.

(10) Patent No.: US 10,301,626 B2
(45) Date of Patent: May 28, 2019

(54) CATALYTIC STRANDS OF MINIMAL HAMMERHEAD RIBOZYMES AND METHODS OF USING THE SAME

(71) Applicant: THE REGENTS OF THE UNIVERSITY OF CALIFORNIA, Oakland, CA (US)

(72) Inventors: Sara Marie O'Rourke, Santa Cruz, CA (US); William Gregory Scott, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/554,660

(22) PCT Filed: Mar. 1, 2016

(86) PCT No.: PCT/US2016/020258
§ 371 (c)(1),
(2) Date: Aug. 30, 2017

(87) PCT Pub. No.: WO2016/140967
PCT Pub. Date: Sep. 9, 2016

(65) Prior Publication Data
US 2018/0080022 A1  Mar. 22, 2018

Related U.S. Application Data

(60) Provisional application No. 62/126,996, filed on Mar. 2, 2015.

(51) Int. Cl.

| | |
|---|---|
| *C12N 15/113* | (2010.01) |
| *A61K 31/70* | (2006.01) |
| *C07H 21/02* | (2006.01) |
| *C07H 21/04* | (2006.01) |
| *C12Q 1/08* | (2006.01) |
| *C12N 15/11* | (2006.01) |

(52) U.S. Cl.
CPC ............ *C12N 15/113* (2013.01); *A61K 31/70* (2013.01); *C07H 21/02* (2013.01); *C07H 21/04* (2013.01); *C12N 15/111* (2013.01); *C12N 15/1132* (2013.01); *C12Q 1/08* (2013.01); *C12N 2310/121* (2013.01); *C12N 2320/13* (2013.01); *C12N 2320/50* (2013.01); *C12N 2320/51* (2013.01)

(58) Field of Classification Search
CPC .. C12N 15/111; C12N 15/113; A01K 2207/05
See application file for complete search history.

(56) References Cited

U.S. PATENT DOCUMENTS

| | | |
|---|---|---|
| 2003/0092651 A1 | 5/2003 | Norris et al. |
| 2006/0121466 A1 | 6/2006 | Khvorova et al. |
| 2014/0228556 A1 | 8/2014 | Fukuda et al. |

FOREIGN PATENT DOCUMENTS

| | | | |
|---|---|---|---|
| WO | WO-9967400 A1 * | 12/1999 | ........... C12N 15/113 |
| WO | WO 2010/127209 | 11/2010 | |
| WO | WO 2014/155320 | 10/2014 | |

OTHER PUBLICATIONS

Scott et al. TIBS 21: 220-224 (Year: 1996).*
Leontis et al. RNA 7:499-512 (Year: 2001).*
Citti et al., "Synthetic Hammerhead Ribozymes as Therapeutic Tools to Control Disease Genes" Current Gene Therapy (2005) 5:11-24.
Hammann et al., "The ubiquitous hammerhead ribozyme" RNA (May 1, 2012) 18:871-85.
Hertel et al., "Numbering system for the hammerhead" Nucleic Acids Research (May 4, 1992) 20(12):3532.
Kashani-Sabet, Mohammed, "Ribozyme Therapeutics" The Society for Investigative Dermatology, Inc. (2002), pp. 76-78.
Martick et al., "Tertiary Contacts Distant from the Active Site Prime a Ribozyme for Catalysis" Cell (Jul. 28, 2006) 126:309-320.
Mitsuyasu et al., "Phase 2 gene therapy trail of an anti-HIV ribozyme in autologous CD34+ cells" Nature Medicine (Mar. 2009) 15(3):285-292.
Mulhbacher et al., "Therapeutic applications of ribozymes and riboswitches" Current Opinion in Pharmacology (2010) 10:551-556.
O'Rourke et al., "Minimal Hammerhead Rlbozyms with Uncompromised Catalytic Activity" Journal of Molecular Biology (Feb. 4, 2015) 427:340-7.
Przybilski et al., "The Hammerhead Ribozyme Structure Brought in Line" ChemBioChem (2006) 7:1641-1644.
Rossi, John J. "Targeted Cleavage: Tuneable cis-cleaving ribozymes" PNAS (Sep. 18, 2007) 104(38):14881-14882.

(Continued)

*Primary Examiner* — Brian Whiteman
(74) *Attorney, Agent, or Firm* — Brian E. Davy; Bozicevic, Field & Francis LLP

(57) ABSTRACT

Provided are minimal hammerhead ribozymes and catalytic strands thereof. Aspects of the present disclosure include a catalytic strand of a minimal hammerhead ribozyme, the catalytic strand including a catalytic core region, a stem I-forming region, a stem II region, and a stem III-forming region. The catalytic strand hybridizes to a target strand via the stem I-forming region and the stem III-forming region. A nucleotide (e.g., an adenine, cytosine, or a natural or non-natural nucleotide base having hydrogen bond donor and acceptor functionalities at positions analogous to those of adenine or cytosine) present in a stem II loop base pairs with a nucleotide (e.g., uracil or cytosine) at position 1.7 of the target strand. Also provided are compositions that include the catalytic strands, and methods of using the catalytic strands, e.g., in a variety of different applications, as well as kits that find use in practicing embodiments of the methods.

20 Claims, 10 Drawing Sheets

Specification includes a Sequence Listing.

(56) References Cited

OTHER PUBLICATIONS

Scott, William G., "What can the New Hammerhead Ribozyme Structures Teach us About Design?" *RNA Technologies and Their Applications*, V.A. Erdmmann and J. Barciszewski (eds), Springer Verlag Berlin Heidelberg (2010) pp. 305-323.

Stage-Zimmerman et al., "Hammerhead ribozyme kinetics" RNA (1998) 4:875-889.

Suyama et al., "Identification of genes involved in cell invasion by using a library of randomized hybrid ribozymes" PNAS (May 13, 2003) 100(10):5616-5621.

Tedeschi et al., "Hammerhead ribozymes in therapeutic target discovery and validation" Drug Discovery Today (Aug. 2009) 14(15/16):776-783.

\* cited by examiner

SEQUENCE LISTING

<160> NUMBER OF SEQ ID NOS: 22

<210> SEQ ID NO 1
<211> LENGTH: 33
<212> TYPE: RNA
<213> ORGANISM: Artificial sequence
<220> FEATURE:
<223> OTHER INFORMATION: Synthetic nucleic acid

<400> SEQUENCE: 1
gacugucuga ugaguccgug aggacgaaac cca          33

<210> SEQ ID NO 2
<211> LENGTH: 21
<212> TYPE: RNA
<213> ORGANISM: Artificial sequence
<220> FEATURE:
<223> OTHER INFORMATION: Synthetic nucleic acid

<400> SEQUENCE: 2
ugggucacag ucuauuaugg g          21

<210> SEQ ID NO 3
<211> LENGTH: 44
<212> TYPE: RNA
<213> ORGANISM: Artificial sequence
<220> FEATURE:
<223> OTHER INFORMATION: Synthetic nucleic acid

<400> SEQUENCE: 3
ggcccauaau agacugucug augaguccgu gaggacgaaa ccca            44

<210> SEQ ID NO 4
<211> LENGTH: 36
<212> TYPE: RNA
<213> ORGANISM: Artificial sequence
<220> FEATURE:
<223> OTHER INFORMATION: Synthetic nucleic acid

<400> SEQUENCE: 4
guugacuguc ugaugagucc gugaggacga aaccca                     36

<210> SEQ ID NO 5
<211> LENGTH: 33
<212> TYPE: RNA
<213> ORGANISM: Artificial sequence
<220> FEATURE:
<223> OTHER INFORMATION: Synthetic nucleic acid

<400> SEQUENCE: 5
gacugucuga ugaguccgua aggacgaaac cca                        33

<210> SEQ ID NO 6
<211> LENGTH: 33
<212> TYPE: RNA
<213> ORGANISM: Artificial sequence
<220> FEATURE:
<223> OTHER INFORMATION: Synthetic nucleic acid

<400> SEQUENCE: 6
gacugucuga ugaguccguu aggacgaaac cca                        33

<210> SEQ ID NO 7
<211> LENGTH: 36
<212> TYPE: RNA
<213> ORGANISM: Artificial sequence
<220> FEATURE:
<223> OTHER INFORMATION: Synthetic nucleic acid

<400> SEQUENCE: 7
guugacuguc ugaugagucc guaaggacga aaccca                     36

<210> SEQ ID NO 8
<211> LENGTH: 36
<212> TYPE: RNA
<213> ORGANISM: Artificial sequence
<220> FEATURE:
<223> OTHER INFORMATION: Synthetic nucleic acid

<400> SEQUENCE: 8
guugacuguc ugaugagucc guuaggacga aaccca                     36

<210> SEQ ID NO 9
<211> LENGTH: 33
<212> TYPE: RNA
<213> ORGANISM: Artificial sequence
<220> FEATURE:
<223> OTHER INFORMATION: Synthetic nucleic acid -continued

```
<400> SEQUENCE: 9
gacugucuga ugaguccgug cggacgaaac cca                          33

<210> SEQ ID NO 10
<211> LENGTH: 35
<212> TYPE: RNA
<213> ORGANISM: Artificial sequence
<220> FEATURE:
<223> OTHER INFORMATION: Synthetic nucleic acid

<400> SEQUENCE: 10
uaccagcuga ugagucccaa auaggacgaa acgcc                        35

<210> SEQ ID NO 11
<211> LENGTH: 22
<212> TYPE: RNA
<213> ORGANISM: Artificial sequence
<220> FEATURE:
<223> OTHER INFORMATION: Synthetic nucleic acid

<400> SEQUENCE: 11
ugggucacag ucuauuaugg gg                                      22

<210> SEQ ID NO 12
<211> LENGTH: 20
<212> TYPE: RNA
<213> ORGANISM: Artificial sequence
<220> FEATURE:
<223> OTHER INFORMATION: Synthetic nucleic acid

<400> SEQUENCE: 12
ggcguccugg uauccaaucc                                         20

<210> SEQ ID NO 13
<211> LENGTH: 31
<212> TYPE: RNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (1)..(6)
<223> OTHER INFORMATION: n may be any nucleotide.
<220> FEATURE:
<221> NAME/KEY: misc_feature
<222> LOCATION: (11)..(11)
<223> OTHER INFORMATION: n may be any nucleotide.
<220> FEATURE:
<221> NAME/KEY: misc_feature
<222> LOCATION: (14)..(20)
<223> OTHER INFORMATION: n may be any nucleotide.
<220> FEATURE:
<221> NAME/KEY: misc_feature
<222> LOCATION: (22)..(25)
<223> OTHER INFORMATION: n may be any nucleotide.
<220> FEATURE:
<221> NAME/KEY: misc_feature
<222> LOCATION: (30)..(30)
<223> OTHER INFORMATION: y may be any pyrimidine.
<220> FEATURE:
<221> NAME/KEY: misc_feature
<222> LOCATION: (31)..(31)
<223> OTHER INFORMATION: n may be any nucleotide.

<400> SEQUENCE: 13
nnnnnncuga ngannnnnnn annnngaaay n                            31

<210> SEQ ID NO 14
<211> LENGTH: 37
```

```
<212> TYPE: RNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (1)..(7)
<223> OTHER INFORMATION: n may be any nucleotide.
<220> FEATURE:
<221> NAME/KEY: misc_feature
<222> LOCATION: (12)..(12)
<223> OTHER INFORMATION: n may be any nucleotide.
<220> FEATURE:
<221> NAME/KEY: misc_feature
<222> LOCATION: (15)..(24)
<223> OTHER INFORMATION: n may be any nucleotide.
<220> FEATURE:
<221> NAME/KEY: misc_feature
<222> LOCATION: (26)..(31)
<223> OTHER INFORMATION: n may be any nucleotide.
<220> FEATURE:
<221> NAME/KEY: misc_feature
<222> LOCATION: (36)..(36)
<223> OTHER INFORMATION: y may be any pyrimidine.
<220> FEATURE:
<221> NAME/KEY: misc_feature
<222> LOCATION: (37)..(37)
<223> OTHER INFORMATION: n may be any nucleotide.

<400> SEQUENCE: 14
nnnnnnncug angannnnnn nnnnannnnn ngaaayn                           37

<210> SEQ ID NO 15
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 15
tgggtcacag tctattatgg g                                            21

<210> SEQ ID NO 16
<211> LENGTH: 14
<212> TYPE: RNA
<213> ORGANISM: Artificial sequence
<220> FEATURE:
<223> OTHER INFORMATION: Synthetic nucleic acid

<400> SEQUENCE: 16
ugggucacag ucua                                                    14

<210> SEQ ID NO 17
<211> LENGTH: 11
<212> TYPE: RNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (1)..(1)
<223> OTHER INFORMATION: n can be any nucleotide.
<220> FEATURE:
<221> NAME/KEY: misc_feature
<222> LOCATION: (2)..(2)
<223> OTHER INFORMATION: r can be any purine.
<220> FEATURE:
<221> NAME/KEY: misc_feature
<222> LOCATION: (4)..(4)
<223> OTHER INFORMATION: h can be any nucleotide except G.
<220> FEATURE:
<221> NAME/KEY: misc_feature
<222> LOCATION: (5)..(10)
```

```
<223> OTHER INFORMATION: n can be any nucleotide.
<220> FEATURE:
<221> NAME/KEY: misc_feature
<222> LOCATION: (11)..(11)
<223> OTHER INFORMATION: y can be any pyrimidine.

<400> SEQUENCE: 17
nruhnnnnnn y                                                              11

<210> SEQ ID NO 18
<211> LENGTH: 12
<212> TYPE: RNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (1)..(1)
<223> OTHER INFORMATION: n can be any nucleotide.
<220> FEATURE:
<221> NAME/KEY: misc_feature
<222> LOCATION: (2)..(2)
<223> OTHER INFORMATION: r can be any purine.
<220> FEATURE:
<221> NAME/KEY: misc_feature
<222> LOCATION: (4)..(4)
<223> OTHER INFORMATION: h can be any nucleotide except G.
<220> FEATURE:
<221> NAME/KEY: misc_feature
<222> LOCATION: (5)..(11)
<223> OTHER INFORMATION: n can be any nucleotide.
<220> FEATURE:
<221> NAME/KEY: misc_feature
<222> LOCATION: (12)..(12)
<223> OTHER INFORMATION: y can be any pyrimidine.

<400> SEQUENCE: 18
nruhnnnnnn ny                                                             12

<210> SEQ ID NO 19
<211> LENGTH: 31
<212> TYPE: RNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (1)..(6)
<223> OTHER INFORMATION: n can be any nucleotide.
<220> FEATURE:
<221> NAME/KEY: misc_feature
<222> LOCATION: (11)..(11)
<223> OTHER INFORMATION: n can be any nucleotide.
<220> FEATURE:
<221> NAME/KEY: misc_feature
<222> LOCATION: (14)..(20)
<223> OTHER INFORMATION: n can be any nucleotide.
<220> FEATURE:
<221> NAME/KEY: misc_feature
<222> LOCATION: (22)..(25)
<223> OTHER INFORMATION: n can be any nucleotide.
<220> FEATURE:
<221> NAME/KEY: misc_feature
<222> LOCATION: (30)..(30)
<223> OTHER INFORMATION: y can be any pyrimidine.
<220> FEATURE:
<221> NAME/KEY: misc_feature
<222> LOCATION: (31)..(31)
<223> OTHER INFORMATION: n can be any nucleotide.

<400> SEQUENCE: 19
nnnnnncuga ngannnnnnn cnnnngaaay n                                        31
```

```
<210> SEQ ID NO 20
<211> LENGTH: 37
<212> TYPE: RNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (1)..(7)
<223> OTHER INFORMATION: n can be any nucleotide.
<220> FEATURE:
<221> NAME/KEY: misc_feature
<222> LOCATION: (12)..(12)
<223> OTHER INFORMATION: n can be any nucleotide.
<220> FEATURE:
<221> NAME/KEY: misc_feature
<222> LOCATION: (15)..(24)
<223> OTHER INFORMATION: n can be any nucleotide.
<220> FEATURE:
<221> NAME/KEY: misc_feature
<222> LOCATION: (26)..(31)
<223> OTHER INFORMATION: n can be any nucleotide.
<220> FEATURE:
<221> NAME/KEY: misc_feature
<222> LOCATION: (36)..(36)
<223> OTHER INFORMATION: y can be any pyrimidine.
<220> FEATURE:
<221> NAME/KEY: misc_feature
<222> LOCATION: (37)..(37)
<223> OTHER INFORMATION: n can be any nucleotide.

<400> SEQUENCE: 20
nnnnnnncug angannnnnn nnnncnnnnn ngaaayn                          37

<210> SEQ ID NO 21
<211> LENGTH: 31
<212> TYPE: RNA
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (1)..(6)
<223> OTHER INFORMATION: n can be any nucleotide.
<220> FEATURE:
<221> NAME/KEY: misc_feature
<222> LOCATION: (11)..(11)
<223> OTHER INFORMATION: n can be any nucleotide.
<220> FEATURE:
<221> NAME/KEY: misc_feature
<222> LOCATION: (14)..(20)
<223> OTHER INFORMATION: n can be any nucleotide.
<220> FEATURE:
<221> NAME/KEY: misc_feature
<222> LOCATION: (21)..(21)
<223> OTHER INFORMATION: n can be any natural or non-natural nucleotide.
<220> FEATURE:
<221> NAME/KEY: misc_feature
<222> LOCATION: (22)..(25)
<223> OTHER INFORMATION: n can be any nucleotide.
<220> FEATURE:
<221> NAME/KEY: misc_feature
<222> LOCATION: (30)..(30)
<223> OTHER INFORMATION: y can be any pyrimidine.
<220> FEATURE:
<221> NAME/KEY: misc_feature
<222> LOCATION: (31)..(31)
<223> OTHER INFORMATION: n can be any nucleotide.

<400> SEQUENCE: 21
nnnnnncuga ngannnnnnn nnnnngaaay n                                31

<210> SEQ ID NO 22
<211> LENGTH: 38
<212> TYPE: RNA
```

```
<213> ORGANISM: Artificial sequence
<220> FEATURE:
<223> OTHER INFORMATION: Synthetic nucleic acid
<220> FEATURE:
<221> NAME/KEY: misc_feature
<222> LOCATION: (1)..(7)
<223> OTHER INFORMATION: n can be any nucleotide.
<220> FEATURE:
<221> NAME/KEY: misc_feature
<222> LOCATION: (12)..(12)
<223> OTHER INFORMATION: n can be any nucleotide.
<220> FEATURE:
<221> NAME/KEY: misc_feature
<222> LOCATION: (15)..(24)
<223> OTHER INFORMATION: n can be any nucleotide.
<220> FEATURE:
<221> NAME/KEY: misc_feature
<222> LOCATION: (25)..(25)
<223> OTHER INFORMATION: n can be any natural or non-natural nucleotide.
<220> FEATURE:
<221> NAME/KEY: misc_feature
<222> LOCATION: (26)..(31)
<223> OTHER INFORMATION: n can be any nucleotide.
<220> FEATURE:
<221> NAME/KEY: misc_feature
<222> LOCATION: (32)..(32)
<223> OTHER INFORMATION: n is a, c, g, or u
<220> FEATURE:
<221> NAME/KEY: misc_feature
<222> LOCATION: (36)..(36)
<223> OTHER INFORMATION: y can be any pyrimidine.
<220> FEATURE:
<221> NAME/KEY: misc_feature
<222> LOCATION: (37)..(37)
<223> OTHER INFORMATION: n can be any nucleotide.
<220> FEATURE:
<221> NAME/KEY: misc_feature
<222> LOCATION: (38)..(38)
<223> OTHER INFORMATION: n is a, c, g, or u

<400> SEQUENCE: 22
nnnnnnncug angannnnnn nnnnnnnnnn nngaaayn                              38
```

US 10,301,626 B2

CATALYTIC STRANDS OF MINIMAL HAMMERHEAD RIBOZYMES AND METHODS OF USING THE SAME

CROSS-REFERENCE TO RELATED APPLICATIONS

This application is a 371 National Phase of International Patent Application Serial No. PCT/US2016/020258 which claims the benefit of U.S. Provisional Patent Application No. 62/126,996, filed Mar. 2, 2015, which applications are incorporated herein by reference in their entirety.

STATEMENT REGARDING FEDERALLY SPONSORED RESEARCH

This invention was made with government support under grant no. R01GM087721 awarded by the National Institutes of Health. The government has certain rights in the invention.

INTRODUCTION

The hammerhead RNA sequence within satellite RNA genomes occurs at the interface of two monomeric segments of a linear concatamer following rolling circle replication. Although it is, in that context, a single self-cleaving strand of RNA that is capable of catalyzing only a single, albeit highly specific, cleavage reaction, the hammerhead RNA can be artificially engineered to create a true multiple-turnover ribozyme simply by separating the molecule into discrete catalytic and target strands. The latter constructs have been studied in vitro and also correspond to hammerhead ribozyme sequences that have been used for targeting other RNAs.

The minimal hammerhead sequence includes a central core region of mostly invariant nucleotides flanked by three A-form Watson-Crick base-paired helical sequences whose detailed sequence is comparatively less important. Minimal hammerhead ribozymes have typical Km values of approximately 10 μm, and turnover rates of about 1 target molecule/minute, whereas full-length hammerhead ribozymes have a similar Km but may be as much as 1,000-fold faster with respect to turnover rate.

SUMMARY

Provided are minimal hammerhead ribozymes and catalytic strands thereof. Aspects of the present disclosure include a catalytic strand of a minimal hammerhead ribozyme, the catalytic strand including a catalytic core region, a stem I-forming region, a stem II region, and a stem III-forming region. The catalytic strand hybridizes to a target strand via the stem I-forming region and the stem III-forming region. A nucleotide (e.g., an adenine, cytosine, or a natural or non-natural nucleotide base having hydrogen bond donor and acceptor functionalities at positions analogous to those of adenine or cytosine) present in a stem II loop base pairs with a nucleotide (e.g., uracil or cytosine) at position 1.7 of the target strand. Also provided are compositions that include the catalytic strands, and methods of using the catalytic strands, e.g., in a variety of different applications, as well as kits that find use in practicing embodiments of the methods.

BRIEF DESCRIPTION OF THE FIGURES

FIG. 1, Panel B schematically illustrates a minimal hammerhead ribozyme according to one embodiment of the present disclosure. The ribozyme includes a catalytic strand (NNNNNNNCUGANGANNNNNNNNN-NANNNNNNGAAAYN, SEQ ID NO: 14) of a minimal hammerhead ribozyme according to one embodiment of the present disclosure, hybridized to its target strand (NRUHNNNNNNY, SEQ ID NO: 18). In this example, the stem I forming region of the catalytic strand and target strand includes nucleotide "insertions," such that stem I includes six contiguous base pairs formed between the catalytic (lower) and target (upper) strands, but such base pairs are not formed by contiguous nucleotides of each strand. Similarly, stem II of the catalytic strand includes nucleotide "insertions," such that stem II includes four contiguous base pairs formed between strands of the stem II region of the catalytic strand, but such base pairs are not formed by contiguous nucleotides of the stem II region of the catalytic strand. FIG. 1, Panel C schematically illustrates a minimal hammerhead ribozyme according to one embodiment of the present disclosure. The ribozyme includes a catalytic strand (NNNNNNCUGAN-GANNNNNNNCNNNNGAAAYN, SEQ ID NO: 19) of a minimal hammerhead ribozyme according to one embodiment of the present disclosure, hybridized to its target strand (NRUHNNNNNY, SEQ ID NO:17). FIG. 1, Panel D schematically illustrates a minimal hammerhead ribozyme according to one embodiment of the present disclosure. The ribozyme includes a catalytic strand (NNNNNNNCUGAN-GANNNNNNNNNNCNNNNNNGAAAYN, SEQ ID NO: 20) of a minimal hammerhead ribozyme according to one embodiment of the present disclosure, hybridized to its target strand (NRUHNNNNNNY, SEQ ID NO:18). FIG. 1, Panel E schematically illustrates a minimal hammerhead ribozyme according to one embodiment of the present disclosure. The ribozyme includes a catalytic strand (NNNNNNCUGANGANNNNNNNN<u>N</u>NNNNGAAAYN, SEQ ID NO: 21) of a minimal hammerhead ribozyme according to one embodiment of the present disclosure, hybridized to its target strand (NRUHNNNNNY, SEQ ID NO: 17). FIG. 1, Panel F schematically illustrates a minimal hammerhead ribozyme according to one embodiment of the present disclosure. The ribozyme includes a catalytic strand (NNNNNNNCUGANGANNNNNNNNNN <u>N</u>NNNNNNGAAAYN, SEQ ID NO: 22) of a minimal hammerhead ribozyme according to one embodiment of the present disclosure, hybridized to its target strand (NRUHNNNNNNY, SEQ ID NO: 18). For the ribozymes shown in Panels A-F: N=any nucleotide; N—N=any base pair; R=any purine; Y=any pyrimidine; H in the target strand=any nucleotide except G; and <u>N</u> (bold and underlined) in the catalytic strand=any natural or non-natural nucleotide base having hydrogen bond donor and acceptor functionalities at positions analogous to those of adenine or cytosine (see, e.g., the non-limiting examples shown in panels B and D of FIG. 7).

FIG. 3, Panel B shows the corresponding proposed three dimensional structure, using the same color scheme, based on the coordinates 2QUS in the PDB. The AU trans-Hoogsteen base pair is shown as a close-up in the box in the upper right side of the figure. Nucleotides involved in the elaborate tertiary contact present in 2QUS, but absent in the sequence shown in A, are indicated as light grey, including U2.8, which forms a base triple with the AU Hoogsteen pair. The inset in the lower right shows the corresponding minimal hammerhead ribozyme as observed in the original crystal structures, including 1 HMH. In this case, there are no stabilizing contacts between the tetraloop on the left side of the molecule, and Stem I on the right side.

FIG. 7, Panel A schematically illustrates base-pairing between an adenine of the stem II loop of the catalytic strand and a uracil at position 1.7 of the target strand. FIG. 7, Panel B schematically illustrates base-pairing between a 2,6-diaminopurine of the stem II loop of the catalytic strand and a uracil at position 1.7 of the target strand. FIG. 7, Panel C schematically illustrates base-pairing between a cytosine of the stem II loop of the catalytic strand and a uracil at position 1.7 of the target strand. FIG. 7, Panel D schematically illustrates base-pairing between an isocytosine of the stem II loop of the catalytic strand and a uracil at position 1.7 of the target strand.

DETAILED DESCRIPTION

Figure 1A:
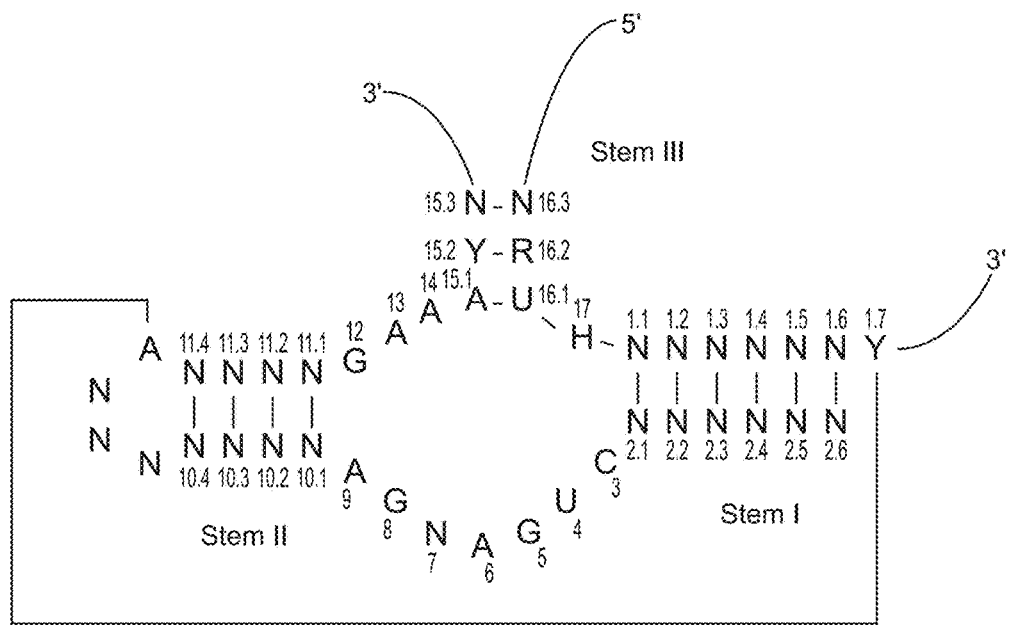
FIG. 1, Panel A schematically illustrates a minimal hammerhead ribozyme according to one embodiment of the present disclosure. The ribozyme includes a catalytic strand (NNNNNNCUGANGANNNNNNNANNNNGAAAYN, SEQ ID NO: 13) of a minimal hammerhead ribozyme according to one embodiment of the present disclosure, hybridized to its target strand (NRUHNNNNNNY, SEQ ID NO: 17).
Figure 1B:
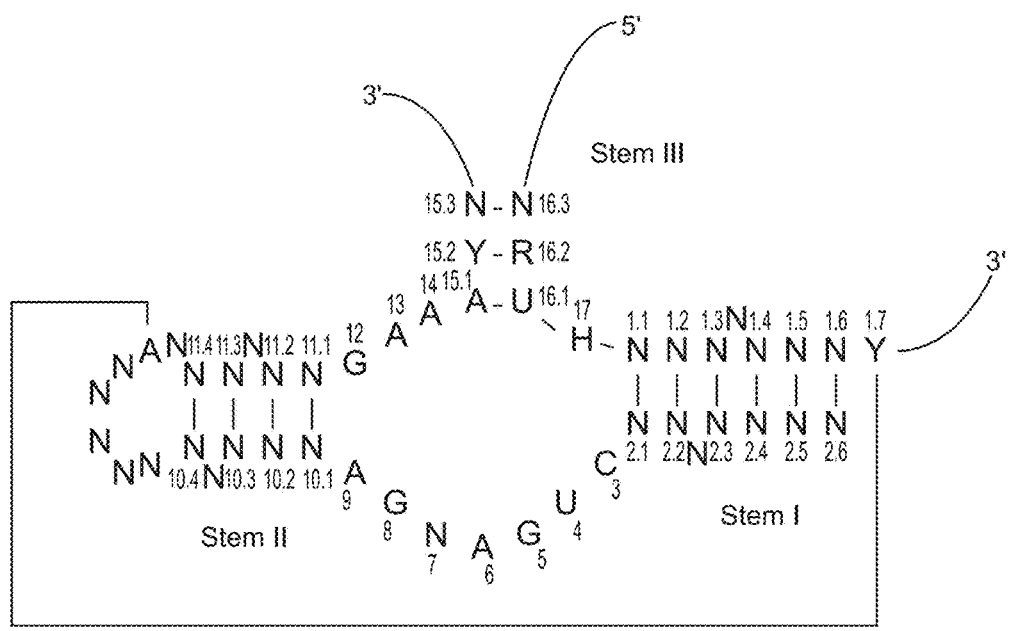
Figure 1C:
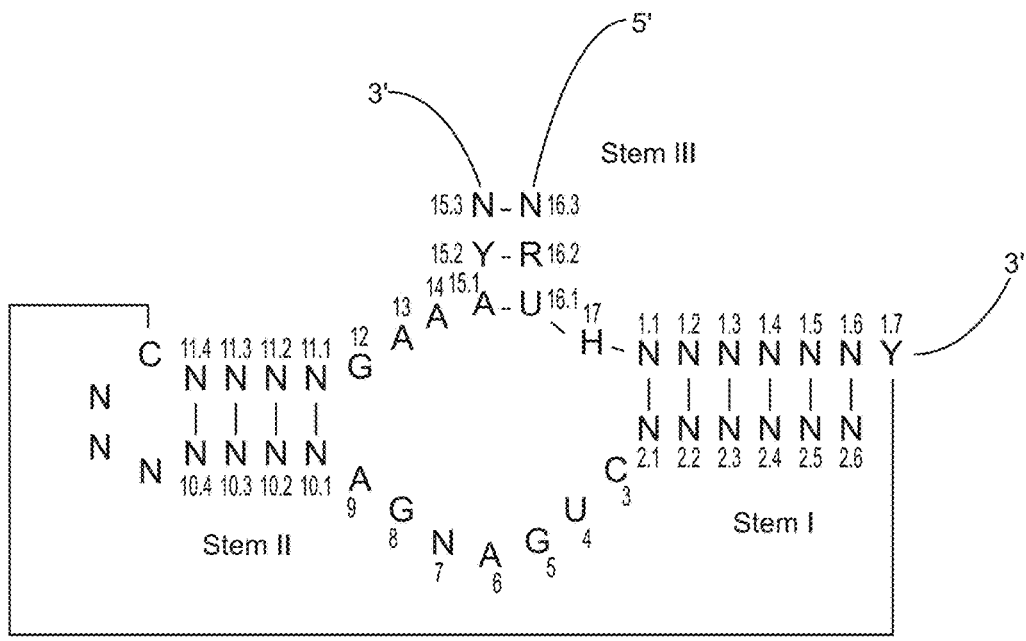
Figure 1D:
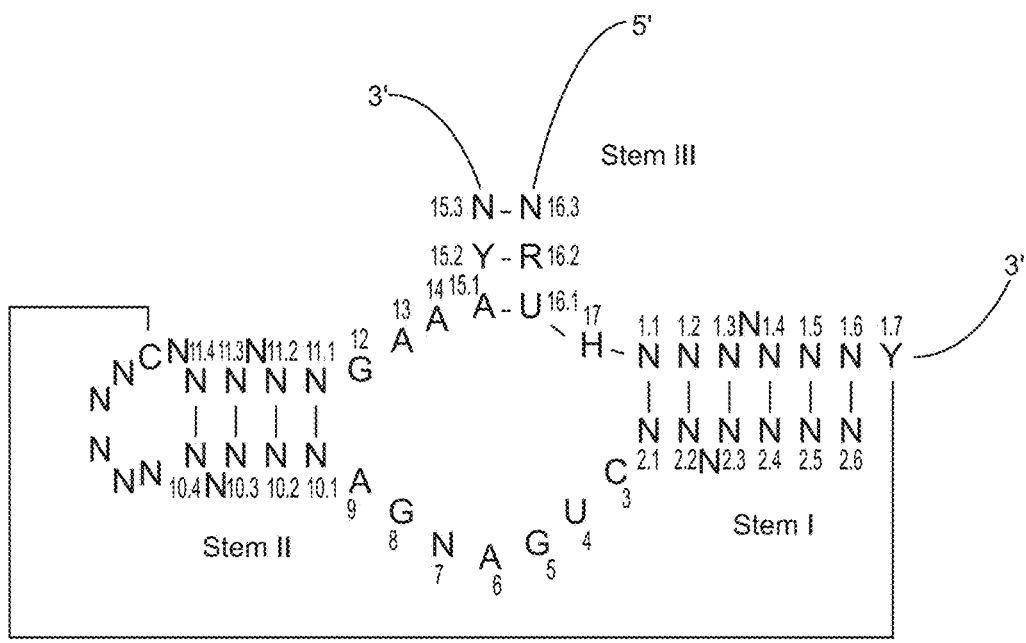
Figure 1E:
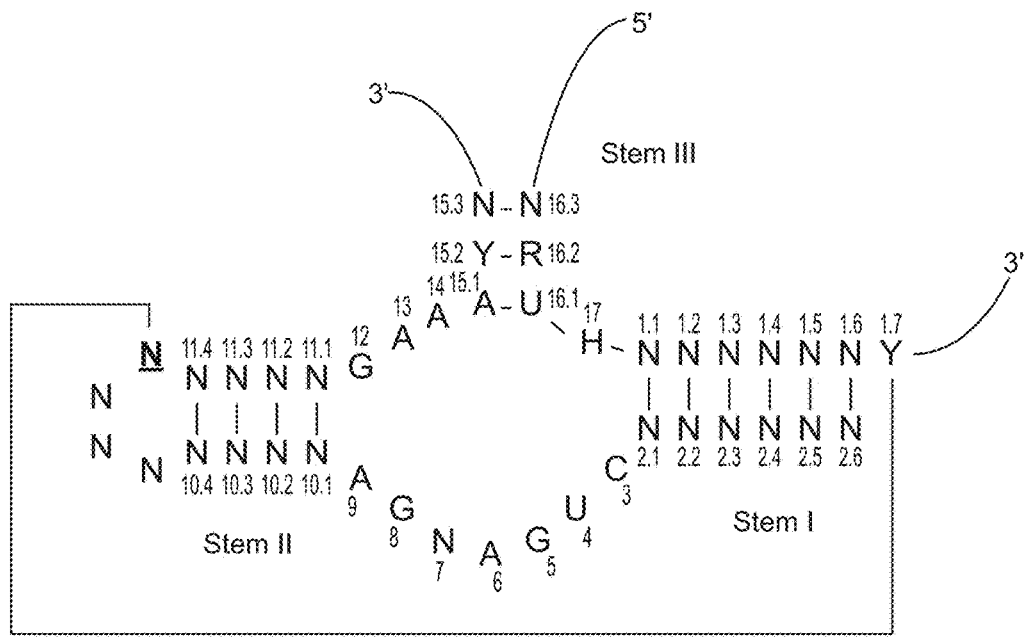
Figure 1F:
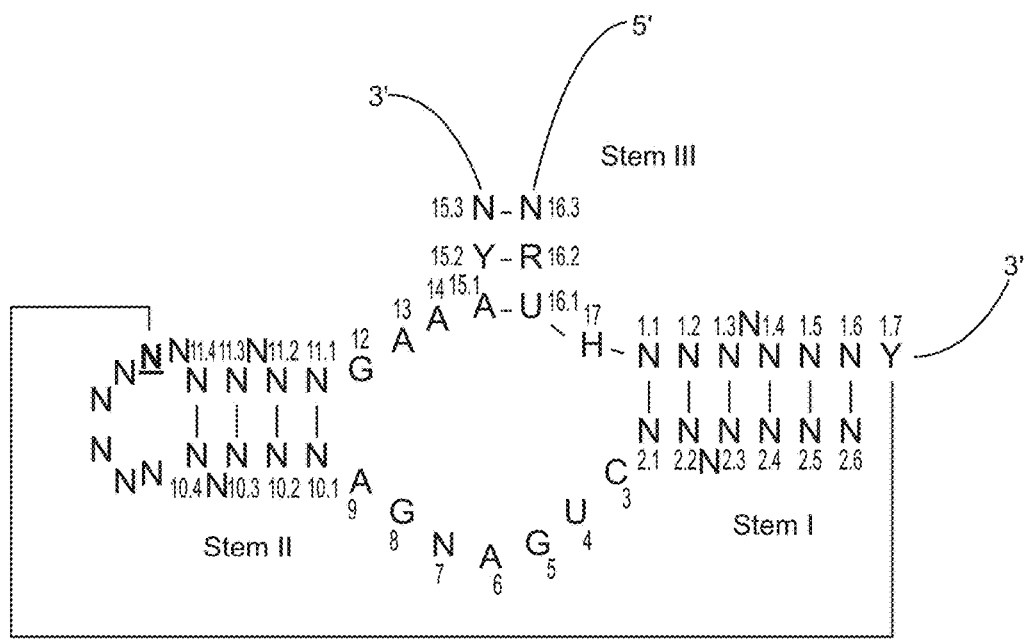

Provided are minimal hammerhead ribozymes and catalytic strands thereof. Aspects of the present disclosure include a catalytic strand of a minimal hammerhead ribozyme, the catalytic strand including a catalytic core region, a stem I-forming region, a stem II region, and a stem III-forming region. The catalytic strand hybridizes to a target strand via the stem I-forming region and the stem III-forming region. A nucleotide (e.g., an adenine, cytosine, or a natural or non-natural nucleotide base having hydrogen bond donor and acceptor functionalities at positions analogous to those of adenine or cytosine) present in a stem II loop base pairs with a nucleotide (e.g., uracil or cytosine) at position 1.7 of the target strand. Also provided are compositions that include the catalytic strands, and methods of using the catalytic strands, e.g., in a variety of different applications, as well as kits that find use in practicing embodiments of the methods.

Before the ribozymes, compositions, and methods of the present disclosure are described in greater detail, it is to be understood that the ribozymes, compositions, and methods are not limited to particular embodiments described, as such may, of course, vary. It is also to be understood that the terminology used herein is for the purpose of describing particular embodiments only, and is not intended to be limiting, since the scope of the ribozymes, compositions, and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the ribozymes, compositions, and methods. The upper and lower limits of these smaller ranges may independently be included in the smaller ranges and are also encompassed within the ribozymes, compositions, and methods, subject to any specifically excluded limit in the stated range. Where the stated range includes one or both of the limits, ranges excluding either or both of those included limits are also included in the ribozymes, compositions, and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the ribozymes, compositions, and methods belong. Although any ribozymes, compositions, and methods similar or equivalent to those described herein can also be used in the practice or testing of the ribozymes, compositions, and methods, representative illustrative ribozymes, compositions, and methods are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present ribozymes, compositions, and methods are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the ribozymes, compositions, and methods, which are, for clarity, described in the context of separate embodiments, may also be provided in combination in a single embodiment. Conversely, various features of the ribozymes, compositions, and methods, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions/kits. In addition, all sub-combinations listed in the embodiments describing such variables are also specifically embraced by the present ribozymes, compositions, and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Catalytic Strands of Minimal Hammerhead Ribozymes

As summarized above, aspects of the present disclosure include minimal hammerhead ribozymes and catalytic strands thereof. For example, catalytic strands of minimal hammerhead ribozymes are provided. As used herein, a "minimal" hammerhead ribozyme is any ribozyme that possesses the conserved catalytic core sequences 5'-CUGANGA-3' and 5'-GAAA-3' as well as three helix-forming sequences of undetermined length and identity, and that has a cleavage rate between 0 and 2 turnovers per minute under standard in vitro reaction conditions (pH 7.5, 10 mM $MgCl_2$). A minimal hammerhead ribozyme of the present disclosure includes the above structural features of a minimal hammerhead ribozyme, and additionally includes a single tertiary interaction, which tertiary interaction (e.g., a trans-Hoogsteen base pair or similar non-Watson Crick base-pairing) is between a nucleotide in the stem II loop of the catalytic strand and a nucleotide at position 1.7 of the target strand, and which tertiary interaction increases the cleavage rate under standard in vitro reaction conditions to 5 turnovers or more per minute.

The catalytic strands include a catalytic core region including the sequence CUGANGA, where N is any nucleotide or a non-nucleotide spacer linkage. In certain aspects, the core region consists of 13, 14, or 15 nucleotides.

The catalytic strands further include a stem I-forming region and a stem III-forming region. The nucleotide content (e.g., the identity and number of nucleotides) of the stem I-forming region may vary. In certain aspects, the stem I-forming region is designed to form from 3 to 6 (e.g., 3, 4, 5 or 6) contiguous base pairs with the target strand. Similarly, the nucleotide content (e.g., the identity and number of nucleotides) of the stem III-forming region may vary. According to certain embodiments, the stem III-forming region is designed to form from 3 to 50, from 3 to 30, from 3 to 20, from 3 to 15, from 3 to 10 or from 3 to 5 contiguous base pairs with the target strand. According to certain embodiments, the stem III-forming region is from 3 to 50, from 3 to 30, from 3 to 20, from 3 to 15, from 3 to 10 or from 3 to 5 nucleotides in length.

According to certain embodiments, the catalytic strand is that of a sTRSV+-like Class III ribozyme. In other aspects, the catalytic strand is that of a Class I hammerhead ribozyme (e.g., a Smα1-like 3ZP8-crystallized hammerhead ribozyme).

The catalytic strand hybridizes to a target strand via the stem I-forming region and the stem III-forming region under hybridization conditions. "Hybridization conditions" include conditions in which the stem I- and stem-III forming regions (collectively) of the catalytic strand specifically hybridize to a target region of the target nucleic acid strand. Whether the catalytic strand specifically hybridizes to a target strand of interest is determined by such factors as the degree and length of complementarity between the catalytic strand and the target strand, and the temperature at which the hybridization/contacting occurs, which may be informed by the melting temperature ($T_M$) of the stem I- and stem-III forming regions of the catalytic strand that are complementary to the target regions of the target nucleic acid strand. The melting temperature refers to the temperature at which half of the stem I-/stem III-forming region-target strand duplexes remain hybridized and half of the duplexes dissociate into single strands. The $T_M$ of a duplex may be experimentally determined or predicted using the following formula $T_M=81.5+16.6(\log_{10}[Na^+])+0.41$ (fraction G+C)–(60/N), where N is the chain length and $[Na^+]$ is less than 1 M. See Sambrook and Russell (2001; Molecular Cloning: A Laboratory Manual, 3rd ed., Cold Spring Harbor Press, Cold Spring Harbor N.Y., Ch. 10). Other more advanced models that depend on various parameters may also be used to predict $T_M$ of stem I-/stem III-forming region-target strand duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, Part I, chapter 2, "Overview of principles of hybridization and the strategy of nucleic acid probe assays," Elsevier (1993).

By "specific hybridization" or "specifically hybridizes" in the context of the catalytic strands of minimal hammerhead ribozymes of the present disclosure refers to the ability of a catalytic strand to preferentially hybridize to a particular strand (the "target" strand) that is present in a homogeneous mixture of different nucleic acid strands. In certain embodiments, the specific hybridization discriminates between target and non-target strands in a sample or organism (e.g., a human), in some embodiments more than about 10 to 100-fold or more (e.g., more than about 1000- or 10,000-fold).

Accordingly, the nucleotide sequences of the stem I- and stem III-forming regions may be designed/predetermined to achieve specificity for a target nucleic acid strand of interest, such that the catalytic strand specifically hybridizes to, and cleaves, the target strand. The hybridization conditions may vary depending upon the application in which a catalytic strand of the present disclosure is employed, and include in vitro conditions of interest and in vivo (e.g., intracellular) conditions of interest.

In certain aspects, regions of complementarity between the catalytic strand and the target nucleic acid strand are based on base pairing between contiguous nucleotides of the catalytic strand and the target strand (see FIG. 1, Panel A). In other aspects, one or both of the catalytic strand and the target strand include "insertions" such that contiguous base pairs are formed between the catalytic strand and the target strand, but not by completely contiguous stretches of nucleotides of the catalytic strand and/or target strand (see FIG. 1, Panel B).

As summarized above, the catalytic strands of the present disclosure include a stem II region that includes helical strands, and a stem II loop that connects the helical strands of the stem II region. The nucleotide content (e.g., the identity and number of nucleotides) of the stem II region may vary. In certain aspects, the stem II region includes from 2 to 6 base pairs (e.g., 2, 3, 4, 5, or 6 base pairs). Such base pairs may be formed between contiguous nucleotides of the respective helical strands of the stem II region (see FIG. 1, Panel A), or one or both of the helical strands of the stem II region may include "insertions" such that contiguous base pairs are formed between the helical strands, but not by completely contiguous stretches of nucleotides of the helical strands (see FIG. 1, Panel B).

The nucleotide content (e.g., the identity and number of nucleotides) of the stem II loop may vary. According to certain embodiments, the stem II loop includes from 2 to 30, from 2 to 20, from 2 to 15 or from 2 to 10 (e.g., 2, 3, 4, 5, 6, 7, 8, 9 or 10) nucleotides that connect the helical strands of the stem II region. In certain aspects, the stem II loop includes an adenine, cytosine, or a natural or non-natural nucleotide base having hydrogen bond donor and acceptor functionalities at positions analogous to those of adenine or cytosine. According to certain embodiments, the stem II loop is a tetraloop (that is, a loop consisting of 4 nucleotides that connect the helical strands of the stem II region). When the stem II loop is a tetraloop, the tetraloop may be a GNRX tetraloop, where: G is a guanine; N is any nucleotide; R is a purine; and X is adenine, cytosine, or a natural or non-natural nucleotide base having hydrogen bond donor and acceptor functionalities at positions analogous to those of adenine or cytosine. According to certain embodiments, R is a guanine. In other embodiments, R is an adenine.

The stem II loop of the catalytic strands of a minimal hammerhead ribozyme of the present disclosure includes a nucleotide that interacts (e.g., forms a trans-Hoogsteen base pair) with a nucleotide at position 1.7 of the target strand. In certain aspects, this base pair interaction occurs between an adenine, cytosine, or a natural or non-natural nucleotide base having hydrogen bond donor and acceptor functionalities at positions analogous to those of adenine or cytosine, in the stem II loop of the catalytic strand and a uracil or cytosine at position 1.7 of the target strand.

In certain embodiments, the base pair interaction between a nucleotide of the stem II loop of the catalytic strand of a minimal hammerhead ribozyme and a nucleotide at position 1.7 of the target strand can occur between an adenine in the stem II loop of the catalytic strand, and a uracil at position 1.7 of the target strand. FIG. 7, panel A, shows a base pair (e.g., trans-Hoogsteen base pair) that is formed between an adenine of the catalytic strand and a uracil at position 1.7 of the target strand. The trans-Hoogsteen base pair allows for the bases to be organized in a certain spatial position and create a certain hydrogen bonding interface.

Any combination of base-pairing between a nucleotide of the stem II loop of the catalytic strand of a minimal hammerhead ribozyme and a nucleotide at position 1.7 of the target strand that preserves the spatial positions of the bases and the hydrogen bonding interface can be employed. For example, FIG. 7, panel B, shows a base-pair between a non-natural nucleotide (in this example, 2,6-diaminopurine) of the stem II loop of the catalytic strand and a uracil at position 1.7 of the target strand.

In certain aspects, a minimal hammerhead ribozyme of the present disclosure can include base-pairing between a cytosine of the stem II loop of the catalytic strand and a uracil at position 1.7 of the target strand (as shown in FIG. 7, panel C). According to certain embodiments, a minimal hammerhead ribozyme of the present disclosure can include base-pairing between an isocytosine of the stem II loop of the catalytic strand and a uracil at position 1.7 of the target strand (as shown in FIG. 7, panel D).

In some aspects, the base-pair interaction between a nucleotide of the stem II loop of the catalytic strand and a nucleotide at position 1.7 of the target strand can occur between an adenine, cytosine, or a natural or non-natural nucleotide base having hydrogen bond donor and acceptor functionalities at positions analogous to those of adenine or cytosine, and a cytosine at position 1.7 of the target strand.

By "position 1.7" of the target strand is meant position 1.7 according to the uniform numbering system for hammerhead ribozymes as described in Hertel et al. (1992) *Nucleic Acids Research* 20(12). Starting with the nucleotide 3' to the cleavage site, the nucleotides in the central core are numbered in a clockwise fashion. Six nucleotides in the core (1.1, 2.1, 10.1, 11.1, 15.1 and 16.1) also receive a decimal to indicate that they are the first nucleotide in the helix.

Figure 2:
FIG. 2 provides an alignment and location of pause site target using the Los Alamos HIV complete filtered Clade B (724 sequence) nucleotide database. For comparison, only two human sequences can be identified in the NCBI data base (ref|AC_000139.1|) with 17/22 nucleotide homology. Sequence on top is SEQ ID NO: 15; sequence on bottom is SEQ ID NO: 11.
Figure 2:
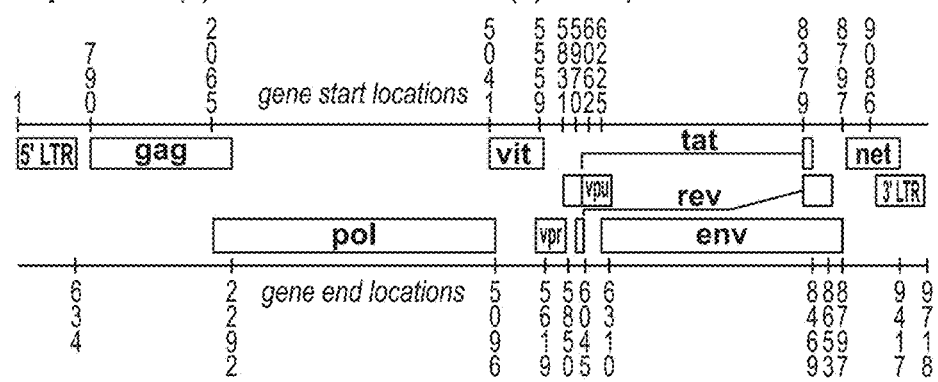

Subsequent residues in the three helices are numbered with sequential decimals extending outward from the core. Unless bulges interrupt the helix, this will result in nucleotides with the same decimal pairing with one another (1.3 pairs with 2.3, 10.4 with 11.4, etc.). If the helices form a hairpin, the single stranded loop is named according to the helix number and the residues are given decimals starting from the 5' side of the loop. This system allows a simple definition of the basic features of any hammerhead. This uniform numbering system is illustrated in the example catalytic and target strands according to embodiments of the present disclosure shown in FIGS. 1A, 1B and 2A.

The present inventors have surprisingly found that designing a catalytic strand of a minimal hammerhead ribozyme to include a nucleotide (e.g., A, C, or a natural or non-natural nucleotide base having hydrogen bond donor and acceptor functionalities at positions analogous to those of A or C) that interacts (e.g., forms a trans-Hoogsteen base pair) with a nucleotide (e.g., U or C when the relevant nucleotide in the stem II loop is an A, C, or a natural or non-natural nucleotide base having hydrogen bond donor and acceptor functionalities at positions analogous to those of A or C) at position 1.7 of the target strand confers upon the catalytic strand a significantly greater nuclease activity and cleavage efficiency as compared to a catalytic strand of a minimal hammerhead ribozyme that does not form such an interaction under identical conditions. For example, a catalytic strand of a minimal hammerhead ribozyme of the present disclosure may exhibit a catalytic activity that is 5-fold or greater, 10-fold or greater, 20-fold or greater, 30-fold or greater, 40-fold or greater, 50-fold or greater, 60-fold or greater, 70-fold or greater, 80-fold or greater, 90-fold or greater, or 100-fold or greater as compared to a catalytic strand of a minimal hammerhead ribozyme that does not form such an interaction under identical conditions. In certain aspects, a catalytic strand of a minimal hammerhead ribozyme of the present disclosure exhibits a catalytic activity that is from 30-fold to 40-fold greater, from 40-fold to 50-fold greater, or from 50-fold to 60-fold greater, as compared to a catalytic strand of a minimal hammerhead ribozyme that does not form such an interaction under identical conditions.

A catalytic strand of a minimal hammerhead ribozyme of the present disclosure may exhibit a cleavage rate such that the catalytic strand cleaves a population of target strands with 50% or greater, 60% or greater, 70% or greater, 80% or greater, 90% or greater, or 95% or greater completeness.

Details of hammerhead ribozyme kinetics and approaches for measuring the catalytic activity, cleavage rates, etc. of hammerhead ribozymes are described, e.g., in Stage-Zimmerman & Uhlenbeck (1998) RNA 4:875-889. The conditions in which catalytic activity, cleavage rates, etc. may be determined include any conditions suitable for catalytic activity of a hammerhead ribozyme. Parameters which may be selected to provide for catalytically active ribozymes include, but are not limited to, pH, $MgCl_2$ concentration, and temperature. According to certain embodiments, the conditions include the standard reaction conditions described in Stage-Zimmerman & Uhlenbeck (1998) RNA 4:875-889, which are pH 7.5, 10 mM $MgCl_2$, and 25° C.

Also provided by the present disclosure is a population of minimal hammerhead ribozyme catalytic strands. The population includes two or more subpopulations of distinct minimal hammerhead ribozyme catalytic strands. The catalytic strands of the two or more subpopulations include a catalytic core region including the sequence CUGANGA, wherein N is any nucleotide or a non-nucleotide spacer linkage. The catalytic strands of the two or more subpopulations further include a stem I-forming region, a stem II region including helical strands, and a stem II loop that connects the helical strands of the stem II region, where in certain aspects, the stem II loop includes an adenine, cytosine, or a natural or non-natural nucleotide base having hydrogen bond donor and acceptor functionalities at positions analogous to those of adenine or cytosine. The catalytic strands of the two or more subpopulations further include a stem III-forming region. The catalytic strand hybridizes to a target strand via the stem I-forming region and the stem III-forming region, and a nucleotide (e.g., an adenine, cytosine, or a natural or non-natural nucleotide base having hydrogen bond donor and acceptor functionalities at positions analogous to those of adenine or cytosine) of the stem II loop base pairs with a nucleotide (e.g., uracil or cytosine) at position 1.7 of the target strand. According to certain embodiments, the two or more subpopulations are adapted to cleave distinct target nucleic acid strands (e.g., are adapted to silence two different genes). In other aspects, the two or more subpopulations are adapted to cleave a same target nucleic acid strand at different locations of the target nucleic acid strand. In some embodiments, the two or more subpopulations are adapted to both cleave distinct target nucleic acid strands and a same target nucleic acid strand at different locations of the target nucleic acid strand. The population of minimal hammerhead catalytic strands finds use, e.g., for "multiplexed" cleavage of one or more target nucleic acids present in a nucleic acid sample or cell of interest.

The catalytic strands of the present disclosure are designed to cleave target nucleic acid strands of interest. The target strand may be any nucleic acid strand that one desires to target for cleavage by the catalytic strand. Target strands of interest include target RNA strands, target DNA strands, and target RNA-DNA hybrid strands.

As described above, the stem I- and stem III-forming regions of the catalytic strand are complementary (e.g., 100% complementary or less than 100% complementary) to respective regions of a target strand of interest. The sequences of the stem I- and stem III-forming regions may be selected to be sufficiently complementary to a target nucleic acid strand of interest to specifically target the catalytic strand to the target strand. The nucleic acid sequences of target strands of interest (e.g., research or therapeutic targets of interest) are readily available from resources such as the nucleic acid sequence databases of the National Center for Biotechnology Information (NCBI), the European Molecular Biology Laboratory-European Bioinformatics Institute (EMBL-EBI), and the like.

Once a target nucleic acid is selected, and based on the available sequence information for the target nucleic acid, a catalytic strand may be designed to: 1) have stem I- and stem III-forming regions sufficiently complementary to a target region of the target nucleic acid for specific hybridization of the catalytic strand and target strand under hybridization conditions; and 2) have a stem II loop that includes a nucleotide capable of base-pairing (e.g., forming a trans-Hoogsteen base pair) with a nucleotide at position 1.7 of the target strand. The minimal hammerhead ribozyme catalytic strand may be designed to have a 5' end beginning exactly at position 2.6, so as to make available the nucleotide at position 1.7 of the target strand for base-pairing with the relevant nucleotide in the stem II loop of the catalytic strand.

According to certain embodiments, the target strand is a target RNA strand, where the RNA is selected from the group consisting of a messenger RNA (mRNA), a micro- RNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, and a telomere RNA.

In certain aspects, the catalytic strands of the present disclosure are used as "research tools," where the catalytic strands may be used to deplete a nucleic acid sample of a particular target nucleic acid in vitro, may be used for in vitro gene silencing upon transfection into a cultured cell (e.g., to study a particular pathway by targeting transcripts of a gene in the pathway), and the like.

In other aspects, the catalytic strands of the present disclosure find use as therapeutic agents, e.g., for in vivo silencing of genes the expression of which is associated with a medical condition (e.g., a disease or disorder). For example, a catalytic strand may be designed to hybridize to, and cleave, a target nucleic acid strand (e.g., a transcript) present in a subject (e.g., in a cell of a subject, in the circulation of the subject, etc.) upon administration of the catalytic strand to the subject for a therapeutic purpose.

In certain aspects, the target strand is an RNA transcribed from a tumor-specific gene or a tumor-associated gene. Tumor-specific genes include genes that are expressed in malignant cells and not expressed in non-malignant cells. Tumor-associated genes are genes expressed in malignant cells with limited expression in cells of normal tissues, genes that are expressed at much higher levels in malignant versus normal cells, or genes that are developmentally expressed.

According to certain embodiments, the target strand is an RNA from a pathogen (e.g., a transcript transcribed from the genome of a pathogen). Pathogens of interest include, but are not limited to, viral pathogens, bacterial pathogens, amoebic pathogens, parasitic pathogens, and fungal pathogens.

Viral target strands of interest include, but are not limited to, a target strand (e.g., a transcript) from Human Papilloma Virus (HPV), Human Immunodeficiency Virus (HIV), Hepatitis B Virus (HBV), Hepatitis A Virus (HAV), Hepatitis C Virus (HCV), Hepatitis D Virus (HDV), Hepatitis E Virus (HEV), Hepatitis F Virus (HFV), Hepatitis G Virus (HGV), Hepatitis H Virus (HHV), Respiratory Syncytial Virus (RSV), Herpes Simplex Virus (HSV), herpes Cytomegalovirus (CMV), herpes Epstein Barr Virus (EBV), Kaposi's Sarcoma-associated Herpes Virus (KSHV), JC Virus (JCV), myxovirus, rhinovirus, coronavirus, flavivirus West Nile, St. Louis Encephalitis flavivirus, Tick-borne encephalitis flavivirus, Murray Valley encephalitis flavivirus, dengue flavivirus, Simian Virus 40 (SV40), Human T Cell Lymphotropic Virus (HTLV), Moloney-Murine Leukemia Virus (Mo-MuLV), encephalomyocarditis virus (EMCV), measles virus (MV), Varicella zoster virus (VZV), adenovirus, yellow fever virus (YFV), poliovirus or poxvirus.

In certain aspects, the target strand is from Human Immunodeficiency Virus (HIV). According to certain embodiments, the target strand is a transcript transcribed from an HIV gene. Target strands of interest include those transcribed from genes that encode structural proteins (e.g., gag, pol or env), regulatory elements (e.g., tat or rev), or accessory regulatory proteins (e.g., vpr, vif, nef, vpu or tev) of HIV.

In some embodiments, the target strand is an mRNA transcript of the HIV-1 envelope protein gene. Cleavage of this mRNA using a catalytic strand of a minimal hammerhead ribozyme would prevent production of the viral coat proteins required for receptor binding. As demonstrated in the Experimental section, the inventors have developed highly active catalytic strands of minimal hammerhead ribozymes that specifically target and cleave a strongly-conserved target sequence identified within the mRNA transcript of the HIV-1 envelope protein gene (see Table 1 and FIGS. 2-4). In certain aspects, the catalytic strand that targets a transcript of the HIV-1 envelope protein gene includes or consists of the sequence:

5'-GACUGUCUGAUGAGUCCGUGAGGACGAAAC-CCA-3' (SEQ ID NO: 1), or functional variants thereof.

Such a catalytic strand or variants thereof may be used to form a minimal hammerhead ribozyme with, and cleave, a target strand that includes the sequence:

5'-UGGGUCACAGUCUAUUAUGGG-3' (SEQ ID NO:2), or variants thereof capable of being cleaved by the catalytic strand.

The catalytic strands of minimal hammerhead ribozymes of the present disclosure may be any suitable length. In certain aspects, the catalytic strand is from 30 to 100 nucleotides in length, including from 30 to 90, from 30 to 80, from 30 to 70, from 30 to 60, from 30 to 50, or from 30 to 40 nucleotides in length.

As used herein, the term "nucleotide" generally refers to a phosphate ester of a nucleoside, either as a monomer or within a dinucleotide, oligonucleotide or polynucleotide. A nucleoside generally is a purine base or a pyrimidine base linked to the C-1' carbon of a ribose (a ribonucleoside) or of a deoxyribose (deoxyribonucleoside). Naturally occurring purine bases generally include adenine (A) and guanine (G). Naturally occurring pyrimidine bases generally include cytosine (C), uracil (U) and thymine (T). When the nucleoside base is a purine, the ribose or deoxyribose is attached to the nucleobase at the 9-position of the purine, and when the nucleobase is a pyrimidine, the ribose or deoxyribose is attached to the nucleobase at the 1-position of the pyrimidine. A ribonucleotide is a phosphate ester of a ribonucleoside and a deoxyribonucleotide is a phosphate ester of a deoxyribonucleoside. The term "nucleotide" is generic to both ribonucleotides and deoxyribonucleotides.

Nucleotide monomers are linked by internucleoside or internucleotide linkages, e.g., phosphodiester linkages where, as used herein, the term "phosphodiester linkage" refers to phosphodiester bonds or bonds including phosphate analogs thereof, including associated counterions, e.g., $H^+$, $NH_4^+$, $Na^+$, if such counterions are present. Further internucleoside or internucleotide linkages are described below. A dinucleotide generally has two nucleotides covalently bonded via a 3'-5' phosphodiester linkage. An oligonucleotide generally has more than two nucleotides and a polynucleotide generally refers to polymers of nucleotide monomers.

The catalytic strands of the present disclosure may employ natural nucleotides or non-natural nucleotides (e.g., nucleotides that include non-natural modifications, non-natural nucleotide derivatives, and the like). According to certain embodiments, the catalytic strand includes 1 or more non-natural nucleotides, where the 1 or more non-natural nucleotides include a modified sugar portion, a modified base portion, a modified internucleoside portion, or any combination thereof. In certain aspects, the non-natural nucleotide(s) confer upon the catalytic strand a property selected from enhanced stability (such as nuclease resistance, e.g., ribonuclease resistance), increased serum half-life upon administration to a subject, enhanced cellular uptake (see, e.g., U.S. Pat. No. 7,494,982), reduced "off-target" events (i.e., any catalytic event other than catalysis of the target nucleic acid strand; see U.S. Patent Application Publication No. US2014/0094501), and any combinations thereof, relative to a catalytic strand not including the 1 or more non-natural nucleotides.

Modifications to the sugar moiety of a nucleotide that confer nuclease resistance include, but are not limited to, 2'-O methyl, 2'-amino, 2'-fluoro, 2'-deoxy, 2'-O allyl, 2'-allyl, 2'-methylene, 2'-difluoromethylene, and any combinations thereof. Such modifications are described, e.g., in: Sproat, B. S. (1996) Synthetic catalytic oligonucleotides based on the hammerhead ribozyme. In "Catalytic RNA", F. Eckstein and D. M. J. Lilley Ed.s, Nucleic Acids and Molecular Biology, Vol. 10, Springer-Verlag, Berlin, Heidelberg, New York. pp 265-281; Biegelman et al. (1995) New structural motives for hammerhead ribozymes. Catalytic activity of abasic nucleotide substituted ribozymes. *Nucleosides Nucleotides* 14: 907-910; and Heidenreich et al. (1994) High activity and stability of hammerhead ribozymes containing 2'-modified pyrimidine nucleosides and phosphorothioates. *J. Biol. Chem.* 269:2131-2138.

Modifications to the base portion of a nucleotide that confer nuclease resistance include, but are not limited to, abasic nucleotide substitutions, 6-aza and 6-methylpyrimidine ribonucleotides, 2'-NH2 substitutions, 2'-C-allyl substitutions, and any combinations thereof. Catalytically active, nuclease resistant ribozymes having modified bases include those described in Biegelman et al. (1995) *Nucleosides Nucleotides* 14: 907-910; Biegelman et al. (1995) *Nucleosides Nucleotides* 14: 895-899; and Biegelman et al. (1995) *J. Biol. Chem.* 270(43):25702-8. According to certain embodiments, nucleotides include modified base portions including, but not limited to, pyrimidine nucleobases and purine nucleobases, and derivatives and analogs thereof, including but not limited to, pyrimidines and purines substituted by one or more of an alkyl, caboxyalkyl, amino, hydroxyl, halo (i.e., fluoro, chloro, bromo, or iodo), thiol or alkylthiol moiety. Alkyl (e.g., alkyl, caboxyalkyl, etc.) moieties comprise from 1 to 6 carbon atoms. Further modified nucleotides contemplated herein include an oxetane-modified base.

One or more nucleotides of the catalytic strands of the present disclosure may include a modified internucleoside linker portion for enhanced stability. Such modifications may include, but are not limited to, phosphorothioate, phosphorodithioate, phosphoroselenoate, phosphorodiselenoate, phosphoroanilothioate, phosphoranilidate, phosphoramidate, boronophosphates, thioformacetal (—S—CH2-O—CH2-), methylene(methylimino), dimethylhydrazino, phosphoryl linked morpholino, —CH2-CO—NH—CH2-, —CH2-NH—CO—CH2-, and any analogs of phosphate wherein the phosphorus atom is in the +5 oxidation state and one or more of the oxygen atoms is replaced with a non-oxygen moiety, e.g., sulfur. A peptide nucleic acid is a nucleic acid analog in which the backbone comprises synthetic peptide like linkages (amide bonds) usually formed from N-(2-amino-ethyl)-glycine units, resulting in an achiral and uncharged molecule. Phosphate analogs include associated counterions, e.g., $H^+$, $NH_4^+$, $Na^+$, if such counterions are present.

As used herein, a "pyrimidine" may be a natural pyrimidine, or a pyrimidine derivative or pyrimidine analog including, but not limited to, bromothymine, 1-methylpseudouracil, 2-thiouracil, 2-thiothymine, 2-thiocytosine, 2-thiopyrimidine, 2-hydroxy-5-methyl-4-triazolopyridine, 3-methylcytosine, 3-(3-amino-3-carboxy-propyl)uracil, 4-acetylcytosine, 4-thiouracil, N4,N4-ethanocytosine, 4-(6-aminohexylcytosine), 5-methylcytosine, 5-ethylcytosine, 5-(C3,C6)-alkynylcytosine, 5-bromouracil, 5-(carboxyhydroxymethylluracil, 5-carboxymethylaminomethyl-2-thiouracil, 5-chlorouracil, 5-ethyluracil, 5-fluorouracil, 5-iodouracil, 5-propyluracil, 5-propynyluracil, thiouracil, 5-carboxymethylaminomethyluracil, 5-methylaminomethyluracil, 5-methoxyaminomethyl-2-thiouracil, 5-methoxycarbonylmethyluracil, 5-methoxyuracil, uracil-5-oxyacetic acid-methylester, uracil-5-oxyacetic acid, 5-methyl-2-thiouracil, 5-iodo-2'-deoxyuracil, 5-fluorouracil, 5-methyluracil, tricyclic carbazole-based pyrimidine analogs, tricyclic phenoxazine-based pyrimidine analogs, isocytosine, pseudoisocytosine, dihydrouracil, pseudouracil and universal nucleotides.

By "purine" is a meant a natural purine, or a purine derivative or purine analog including, but not limited to, azapurine, azaguanine, azaadenine, deazapurine, deazaguanine, deazaadenine, 1-methylguanine, 1-methyladenine, 1-methylinosine, 2-aminopurine, 2-chloro-6-aminopurine, 2,2-dimethylguanine, 2-methyladenine, 2-methylguanine, 2-methylthio-N6-isopentenyladenine, 2,6-diaminopurine, 6-aminopurine, 6-thioguanine, 6-thioadenine, 6-thiopurine, 6-hydroxyaminopurine, N6-methyladenine, N,N-diemethyladenine, N6-isopentenyladenine, N6,N6-ethano-2,6-diaminopurine, 7-deazaxanthine, 7-deazaguanine, 7-methylguanine, 7-halo-7-deaza purine where halo is bromo, fluoro, iodo or chloro, 7-propyne-7-deaza purine, 8-bromoadenine, 8-hydroxyadenine, 8-bromoguanine, 8-chloroguanine, 8-aminoguanine, 8-hydroxyguanine, 8-methylguanine, 8-thioguanine, 8-oxo-N6-methyladenine, N-((9-β-D-ribofuranosylpurine-6-yl)-carbamoyl)threonine, methylthioadenine, xanthine, hypoxanthine, inosine, wybutoxosine, wybutosine, isoguanine, queuosine, β-D-mannosylqueuosine, β-D-galactosylqueuosine, and universal nucleotides.

Methods of Making Catalytic Strands of Minimal Hammerhead Ribozymes

Also provided are methods of making the catalytic strands of a minimal hammerhead ribozyme of the present disclosure. Any suitable nucleic acid synthesis methods may be employed to make any of the catalytic strands of the present disclosure. For example, the catalytic strands of the present disclosure may be produced in a cell-free system, such as by in vitro transcription. In certain aspects, the catalytic strands are synthesized by RNA polymerase runoff transcription using a DNA template that encodes the catalytic strand of interest. The catalytic strands may be transcribed in a reaction mixture that includes a suitable polymerase (e.g., T7 RNA polymerase), NTPs, a suitable buffer (e.g., Tris-HCl, or the like), a cofactor for the polymerase (e.g., $MgCl_2$), and any other desirable reaction components, such as inorganic pyro-phosphatase, spermidine, DTT, and the like. An agent that destroys the DNA template (e.g., DNase I) may be added following the transcription step. The transcribed catalytic strands may then be purified using a suitable purification strategy, such a purification on a denaturing PAGE gel following by ethanol precipitation, and resuspension in a suitable medium (e.g., water). An example in vitro transcription-based approach for producing the catalytic strands of the present disclosure is provided in the Experimental section below.

Catalytic strands of the present disclosure may also be produced using a solid-phase synthesis approach where synthesis of the catalytic strand is carried out on a solid support. Suitable solid phase synthesis approaches are known and include, e.g., the phosphoramidite method. Phosphoramidite nucleic acid synthesis proceeds in the 3'- to 5'-direction (opposite to the 5'- to 3'-direction of DNA biosynthesis in DNA replication). One nucleotide is added per synthesis cycle. The phosphoramidite DNA synthesis cycle consists of a series of steps that may include ditritylation, activation and coupling, capping, oxidation, detritylation, repeating the previous steps, cleavage of the desired nucleic acid from the solid support, and deprotection. Details regarding the solid-phase synthesis of nucleic acids may be found, e.g., in Southern et al. (1994) *Nucleic Acids Research* 22:1368-1373, Pease et al. (1994) PNAS 91:5022-5026, etc.

According to certain embodiments, the catalytic strands of minimal hammerhead ribozymes of the present disclosure are produced in a host cell. In certain aspects, a recombinant DNA method is used for production of a catalytic strand of the present disclosure. For example, a nucleic acid that encodes the catalytic strand may be inserted into an expression vector. The DNA segment encoding the catalytic strand is operably linked to a control sequence in the expression vector that ensures the transcription of the catalytic strands in the host cell. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for transcription (e.g., high level transcription) of the catalytic strands. Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a polynucleotide encoding a catalytic strand of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express the catalytic strands of the present disclosure. Suitable mammalian host cells include CHO cell lines, various Cos cell lines, HeLa cells, myeloma cell lines, etc. Expression vectors for these cells can include expression control sequences, such as an origin of replication, a promoter, and an enhancer, and necessary processing information sites, such as transcriptional terminator sequences. Examples of suitable expression control sequences are promoters derived from immunoglobulin genes, SV40, adenovirus, bovine papilloma virus, cytomegalovirus, and the like. Once the catalytic strands are expressed, the catalytic strands may be isolated from the cells and purified using any suitable RNA isolation and purification procedures.

Nucleic Acids and Cells

Also provided are nucleic acids that encode any of the catalytic strands of a minimal hammerhead ribozyme of the present disclosure. According to certain embodiments, the nucleic acid is operably linked to one or more regulatory elements, such as a promoter and enhancer, that allow transcription of the catalytic strand in an environment of interest, such as an in vitro cell-free environment, in a cultured cell (e.g., a cell that is genetically modified to synthesize the catalytic strand), in vivo in the cell of a subject (e.g., a mammalian subject, such as a rodent (e.g., a mouse, rat, etc.), a human subject, etc.). Suitable promoter and enhancer elements are known in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 2004/0131637), a pagC promoter (Pulkkinen and Miller, J. Bacteriol., 1991: 173(1): 86-93; Alpuche-Aranda et al., PNAS, 1992; 89(21): 10079-83), a nirB promoter (Harborne et al. (1992) Mol. Micro. 6:2805-2813), and the like (see, e.g., Dunstan et al. (1999) Infect. Immun. 67:5133-5141; McKelvie et al. (2004) Vaccine 22:3243-3255; and Chatfield et al. (1992) Biotechnol. 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO1996/17951); an actA promoter (see, e.g., Shetron-Rama et al. (2002) Infect. Immun. 70:1087-1096); an rpsM promoter (see, e.g., Valdivia and Falkow (1996). Mol. Microbiol. 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al. (1984) Nucl. Acids Res. 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is within the level of ordinary skill in the art.

A nucleotide sequence encoding a catalytic strand of the present disclosure may be present in an expression vector and/or a cloning vector. Such vectors can include a selectable marker, an origin of replication, and other features that provide for replication and/or maintenance of the vector in a host cell. Large numbers of suitable vectors and promoters are known; many are commercially available for generating recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5. Eukaryotic: pWLneo, pSV2cat, pOG44, PXR1, pSG (Stratagene) pSVK3, pBPV, pMSG and pSVL.

The vectors generally have convenient restriction sites located near the promoter sequence to provide for the insertion of nucleic acid sequences encoding a catalytic strand of the present disclosure. A selectable marker operative in the expression host may be present. Suitable expression vectors include, but are not limited to, viral vectors (e.g. viral vectors based on vaccinia virus; poliovirus; adenovirus; adeno-associated virus; SV40; herpes simplex virus; human immunodeficiency virus; a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Also provided are cells that are genetically modified to include a catalytic strand of the present disclosure, or are genetically modified to include a nucleic acid that encodes a catalytic strand of the present disclosure (which nucleic acid may be present in an expression and/or cloning vector). The cells may be present in an environment of interest, such as a cell culture medium, a subject (e.g., a mammalian subject, such as a rodent or human subject), etc.

Suitable host cells include eukaryotic host cells, such as a mammalian cell, an insect host cell, a yeast cell; and prokaryotic cells, such as a bacterial cell. Introduction of the nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) J. Immunol. 148:1176-1181; U.S. Pat. No. 6,447,784; and Sizemore et al. (1995) Science 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli*.

Compositions

Also provided are compositions that include a catalytic strand of a minimal hammerhead ribozyme of the present disclosure. The compositions may include any of the catalytic strands described herein. In certain aspects, the compositions include a catalytic strand of the present disclosure present in a liquid medium. The liquid medium may be an aqueous liquid medium, such as water, a buffered solution, and the like. One or more additives such as a salt (e.g., NaCl, $MgCl_2$, KCl, $MgSO_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a solubilizing agent, a detergent (e.g., a non-ionic detergent such as Tween-20, etc.), a ribonuclease inhibitor, glycerol, a chelating agent, and the like may be present in such compositions.

Pharmaceutical compositions are also provided. The pharmaceutical compositions include any of the catalytic strands of a minimal hammerhead ribozyme of the present disclosure, and a pharmaceutically-acceptable excipient. The pharmaceutical compositions generally include a therapeutically effective amount of the catalytic strand. By "therapeutically effective amount" is meant a dosage sufficient to produce a desired result, e.g., an amount sufficient to effect beneficial or desired therapeutic (including preventative) results, such as a reduction in a symptom of a disease or disorder associated with a gene from which the target strand is produced (e.g., transcribed), as compared to a control. An effective amount can be administered in one or more administrations.

A catalytic strand of the present disclosure can be incorporated into a variety of formulations for therapeutic administration. More particularly, the catalytic strand can be formulated into pharmaceutical compositions by combination with appropriate, pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the catalytic strands of the present disclosure suitable for administration to a patient (e.g., suitable for human administration) are generally sterile and may further be free of detectable pyrogens or other contaminants contraindicated for administration to a patient according to a selected route of administration.

In pharmaceutical dosage forms, the catalytic strands can be administered in the form of their pharmaceutically acceptable salts, or they may also be used alone or in appropriate association, as well as in combination, with other pharmaceutically active compounds. The following methods and excipients are merely examples and are in no way limiting.

For oral preparations, the catalytic strands can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The catalytic strands can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions that include the catalytic strands may be prepared by mixing the catalytic strands having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

An aqueous formulation of the catalytic strand may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the formulation to modulate the tonicity of the formulation. Example tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 mM.

A surfactant may also be added to the formulation to reduce aggregation and/or minimize the formation of particulates in the formulation and/or reduce adsorption. Example surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Example concentrations of surfactant may range from about 0.001% to about 1% w/v.

A lyoprotectant may also be added in order to protect the catalytic strand against destabilizing conditions during a lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, the pharmaceutical composition includes a catalytic strand of the present disclosure, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

Methods

Methods of using the catalytic strands of the present disclosure are also provided.

In certain aspects, the present disclosure provides methods of cleaving a target nucleic acid strand. Such methods include contacting a target nucleic acid strand with the catalytic strand of a minimal hammerhead ribozyme of the present disclosure under conditions in which the catalytic strand cleaves the target nucleic acid strand. According to certain embodiments, the contacting occurs in a cell-free environment. For example, the contacting step may include combining a nucleic acid sample that includes (or is suspected of including) the target nucleic acid strand, and the catalytic strand, in a reaction mixture under conditions in which the catalytic strand cleaves the target nucleic acid strand. Any conditions suitable for catalytic activity of the catalytic strand of a hammerhead ribozyme may be provided. Parameters which may be selected to provide for catalytically active ribozymes include, but are not limited to, pH (e.g., pH 7.0 to 8.0), $MgCl_2$ concentration (e.g., 5 mM to 20 mM), and temperature (e.g., 20° C. to 40° C.). According to certain embodiments, the conditions include the standard reaction conditions as described in Stage-Zimmerman & Uhlenbeck (1998) *RNA* 4:875-889, which are pH 7.5, 10 mM $MgCl_2$, and 25° C., with any useful variations for the particular application of interest.

According to certain embodiments, the target nucleic acid strand is present in a cell. Such methods find use, e.g., when it is desirable to silence a gene of interest by cleaving transcripts transcribed from the gene of interest upon contacting the transcripts with the catalytic strands of the present disclosure. When the target nucleic acid is present in a cell, the methods of cleaving the target nucleic acid may include introducing the catalytic strand into the cell, e.g., by transient or stable transfection of an expression vector that includes a nucleic acid that encodes the catalytic strand, where the nucleic acid is operably linked to one or more regulatory elements (such as a promoter and enhancer) that allow transcription of the catalytic strand in the cell in which the target strand is present. Introduction of the catalytic strand or a nucleic acid encoding the same into the host cell can be effected, for example by calcium phosphate precipitation, DEAE dextran mediated transfection, liposome-mediated transfection, electroporation, or other known method.

In certain aspects, the target nucleic acid strand is present in a cell of a subject. Such methods find use in therapeutic applications, e.g., when it is desirable to silence a gene of interest in cells of the subject by cleaving transcripts transcribed from a gene associated with a disease or condition upon contacting the transcripts with the catalytic strands of the present disclosure. In this context, the contacting step may include, e.g., administering the catalytic strands of the present disclosure (or nucleic acids encoding the same) to the subject in a therapeutically effective amount.

Also provided are methods that include administering to a subject in need thereof a therapeutically effective amount of any of the catalytic strands of a minimal hammerhead ribozyme of the present disclosure, or any of the pharmaceutical compositions described herein. According to certain embodiments, the subject has a disease or disorder associated with a particular gene, and the methods are effective at silencing the gene in cells of the subject via cleavage of transcripts transcribed from the genes by the catalytic strands of the present disclosure.

The gene associated with a disease or disorder may be an endogenous gene (e.g., a gene normally present in the human genome), or the gene may be a gene of a pathogen with which the subject is infected. By way of example, the subject may be infected with HIV, and the methods may be methods of treating HIV infection in the subject. In certain aspects, such methods include administering to a subject infected with HIV a catalytic strand of a minimal hammerhead ribozyme of the present disclosure that targets an HIV transcript, to treat the HIV infection in the subject. According to certain embodiments, the catalytic strand targets a transcript transcribed from an HIV gene that encodes a structural protein (e.g., gag, po/or env), a regulatory element (e.g., tat or rev), or an accessory regulatory protein (e.g., vpr, vif, nef, vpu or tev). For example, provided are methods of treating HIV infection in a subject, the methods including administering to the subject infected with HIV a catalytic strand that includes (or consists of) the sequence: 5'-GACUGUCUGAUGAGUCCGUGAGGACGAAACCCA-3' (SEQ ID NO: 1) or functional variants thereof, in a therapeutically effective amount to treat the HIV infection in the subject.

According to certain embodiments, a catalytic strand of the present disclosure is administered to a subject in the form of a cell-based therapy. By way of example, in the context of methods of treating a subject infected with HIV, an HIV-1-positive subject may be administered G-CSF for stem cell mobilization, followed by peripheral blood stem cell collection by large-volume apheresis. $CD34^+$ cells may then be selected, cultured and transduced with the catalytic strand of interest or a nucleic acid encoding the same, e.g., any of the catalytic strands described herein suitable for cleaving an HIV transcript, including a catalytic strand having the sequence 5'-GACUGUCUGAUGAGUCCGUGAGGAC-GAAACCCA-3' (SEQ ID NO: 1), or a functional variant thereof. After transduction, the cell product may be washed and infused into the subject in a therapeutically effective amount to treat the HIV infection. Cell-based therapies employing anti-HIV ribozymes are described, e.g., in Mitsuyasu et al. (2009) *Nature Medicine* 15(3):285-292.

The catalytic strands of the present disclosure are administered to an individual using any available method and route suitable for drug delivery, including in vivo and ex vivo methods, as well as systemic and localized routes of administration. Conventional and pharmaceutically acceptable routes of administration include intranasal, intramuscular, intra-tracheal, subcutaneous, intradermal, topical application, ocular, intravenous, intra-arterial, nasal, oral, and other enteral and parenteral routes of administration. Routes of administration may be combined, if desired, or adjusted depending upon the catalytic strand and/or the desired effect. The catalytic strand may be administered in a single dose or in multiple doses. In some embodiments, the catalytic strand is administered orally. In some embodiments, the catalytic strand is administered via an inhalational route. In some embodiments, the catalytic strand is administered intranasally. In some embodiments, the catalytic strand is administered locally. In some embodiments, the catalytic strand is administered ocularly. In some embodiments, the catalytic strand is administered intracranially. In some embodiments, the catalytic strand is administered intravenously. In some embodiments, the catalytic strand is administered by injection, e.g., for systemic delivery (e.g., intravenous infusion) or to a local site.

A variety of subjects are treatable according to the subject methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the hosts will be humans.

By treatment is meant at least an amelioration of the symptoms associated with the pathological condition afflicting the subject, where amelioration is used in a broad sense to refer to at least a reduction in the magnitude of a parameter, e.g. symptom, associated with the pathological condition being treated, such as disease or disorder associated with the expression of a gene, which expression may be silenced by administration of an effective amount of a catalytic strand of the present disclosure. As such, treatment also includes situations where the pathological condition, or at least symptoms associated therewith, are completely inhibited, e.g. prevented from happening, or stopped, e.g. terminated, such that the subject no longer suffers from the pathological condition, or at least the symptoms that characterize the pathological condition.

Dosing is dependent on severity and responsiveness of the disease state to be treated. Optimal dosing schedules can be calculated from measurements of drug accumulation in the body of the patient. The administering physician can determine optimum dosages, dosing methodologies and repetition rates. Optimum dosages may vary depending on the relative potency of individual catalytic strands, and can generally be estimated based on $EC_{50}$s found to be effective in in vitro and in vivo animal models, etc. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, where the catalytic strand is administered in maintenance doses, ranging from 0.01 µg to 100 g per kg of body weight, once or more daily, to once every several months, once every six months, once every year, or at any other suitable frequency.

The therapeutic methods of the present disclosure may include administering a single type of catalytic strand to a subject, or may include administering two or more types of catalytic strands to a subject, where the two or more types of catalytic strands are designed to cleave distinct target nucleic acid strands, e.g., for silencing multiple genes in a subject by administration of a cocktail of different minimal hammerhead ribozyme catalytic strands.

Utility

The minimal hammerhead ribozymes and methods of the present disclosure find use in a variety of applications, including any applications in which it is desirable to cleave a target nucleic acid. Applications of interest include, e.g., research applications and clinical applications (e.g., clinical therapeutic and/or diagnostic applications).

According to certain embodiments, the catalytic strands of the minimal hammerhead ribozymes of the present disclosure—by virtue of the interaction between a nucleotide in the stem II loop of the catalytic strand and a nucleotide at position 1.7 of the target strand—exhibit significantly greater catalytic activity and cleavage efficiency than previously thought possible for minimal hammerhead ribozymes. For example, as shown in the Experimental section below, the catalytic strands of the present disclosure may exhibit 50-fold greater activity than previously believed possible for a minimal hammerhead ribozyme, and exhibit a cleavage rate of greater than 90%.

The enhanced kinetic properties of the catalytic strands of the present disclosure provide a number of advantages in both the research and clinical settings. First, the minimal hammerhead ribozyme catalytic strands of the present disclosure exhibit activity levels and cleavage rates that are similar to their counterpart "full-length" hammerhead ribozyme catalytic strands, but are synthesized more easily and cost-effectively (due to their smaller size) as compared to their full-length counterparts, without compromising catalytic activity levels/cleavage rates. Moreover, the minimal hammerhead ribozyme catalytic strands of the present disclosure—being smaller in size as compared to the corresponding full-length catalytic strands—are less likely to elicit anti-viral RNA immune, interferon, or RNAi responses upon administration to a subject, without compromising catalytic activity levels/cleavage rates.

Kits

As summarize above, the present disclosure provides kits. According to certain embodiments, the kits include any of the minimal hammerhead ribozyme catalytic strands described herein, and instructions for using the catalytic strand to cleave a target nucleic acid strand. In certain aspects, the minimal hammerhead ribozyme catalytic strand is present in a container.

Any other components or reagents useful in employing the catalytic strand may be included in the kits. In certain aspects, the kits include a reaction buffer (e.g., in a concentrated form) suitable for preparing a reaction mixture in which the catalytic strand is capable of cleaving a target strand of interest. Any other useful reagents, e.g., transfection reagents suitable for transfecting a cell with a catalytic strand or nucleic acid encoding the same, may be included.

Also provided are kits that include a therapeutically effective amount any of the minimal hammerhead ribozyme catalytic strands of the present disclosure, or a therapeutically effective amount of a pharmaceutical composition that includes any of the minimal hammerhead ribozyme catalytic strands of the present disclosure. Such kits may include instructions for administering the catalytic strands or the pharmaceutical compositions to a subject in need thereof. The kits may include the catalytic strands or the pharmaceutical compositions present in one or more unit dosages, such as 1, 2, 3, 4, 5, etc. unit dosages.

Components of the kits may be present in separate containers, or multiple components may be present in a single container. A suitable container includes a single tube (e.g., vial), one or more wells of a plate (e.g., a 96-well plate, a 384-well plate, etc.), or the like.

The instructions for practicing the subject methods may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

The following examples are offered by way of illustration and not by way of limitation.

EXPERIMENTAL

Example 1

Minimal Hammerhead Ribozymes with Uncompromised Catalytic Activity

Hammerhead RNAs are small autocatalytic motifs found within satellite RNAs of various plant RNA virus genomes, within the 3'-untranslated regions of various mammalian mRNAs, and within introns of many eukaryotes. The hammerhead RNA catalyzes a self-cleavage reaction via phosphodiester isomerization that involves nucleophilic attack of the C17 2'O upon the adjacent scissile phosphate, producing 2',3'-cyclic phosphate and 5'-hydroxyl termini in the cleavage product. The reaction is in essence the same as the first step of that catalyzed by RNase A. Due to its small size, well-characterized reaction chemistry, known high-resolution three-dimensional structure and intensive biophysical and biochemical investigation, as well as its widespread phylogenetic distribution, the hammerhead RNA is an ideal model system for understanding the most fundamental aspects of the chemistry of ribozyme catalysis.

Figures 3A, 3B:
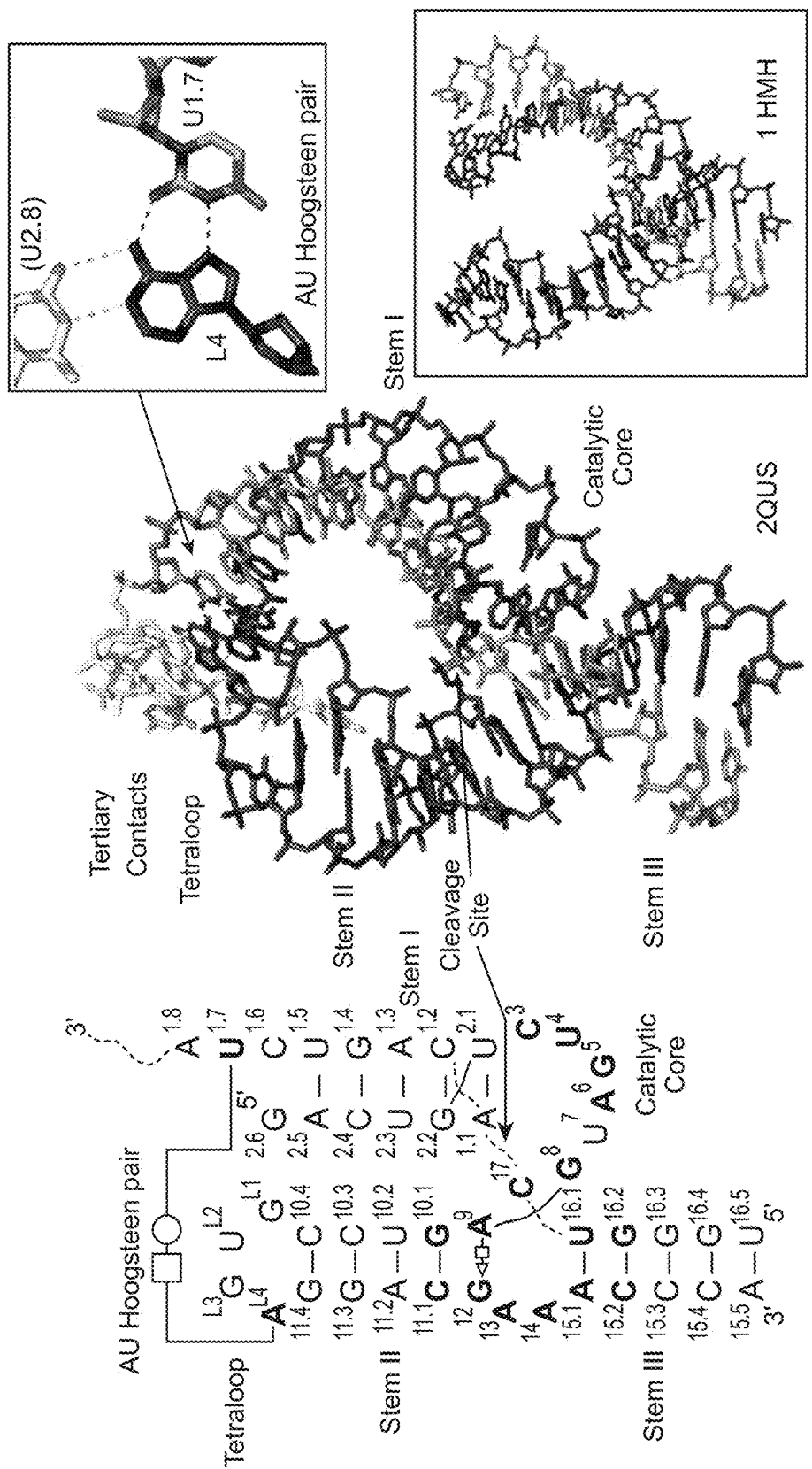
FIG. 3, Panel A shows a secondary structure representation of a minimal ribozyme with high activity ($HH_{min-AL4:U1.7}$) according to one embodiment of the present disclosure. The longer strand is the catalytic strand (SEQ ID NO: 1) and the shorter strand is the target strand (SEQ ID NO: 16). The cleavage site is indicated with an arrow. Invariant and conserved nucleotides in the catalytic core are highlighted in boldface, as is AL4 in the tetraloop and U1.7 in Stem I.
Figure 5:
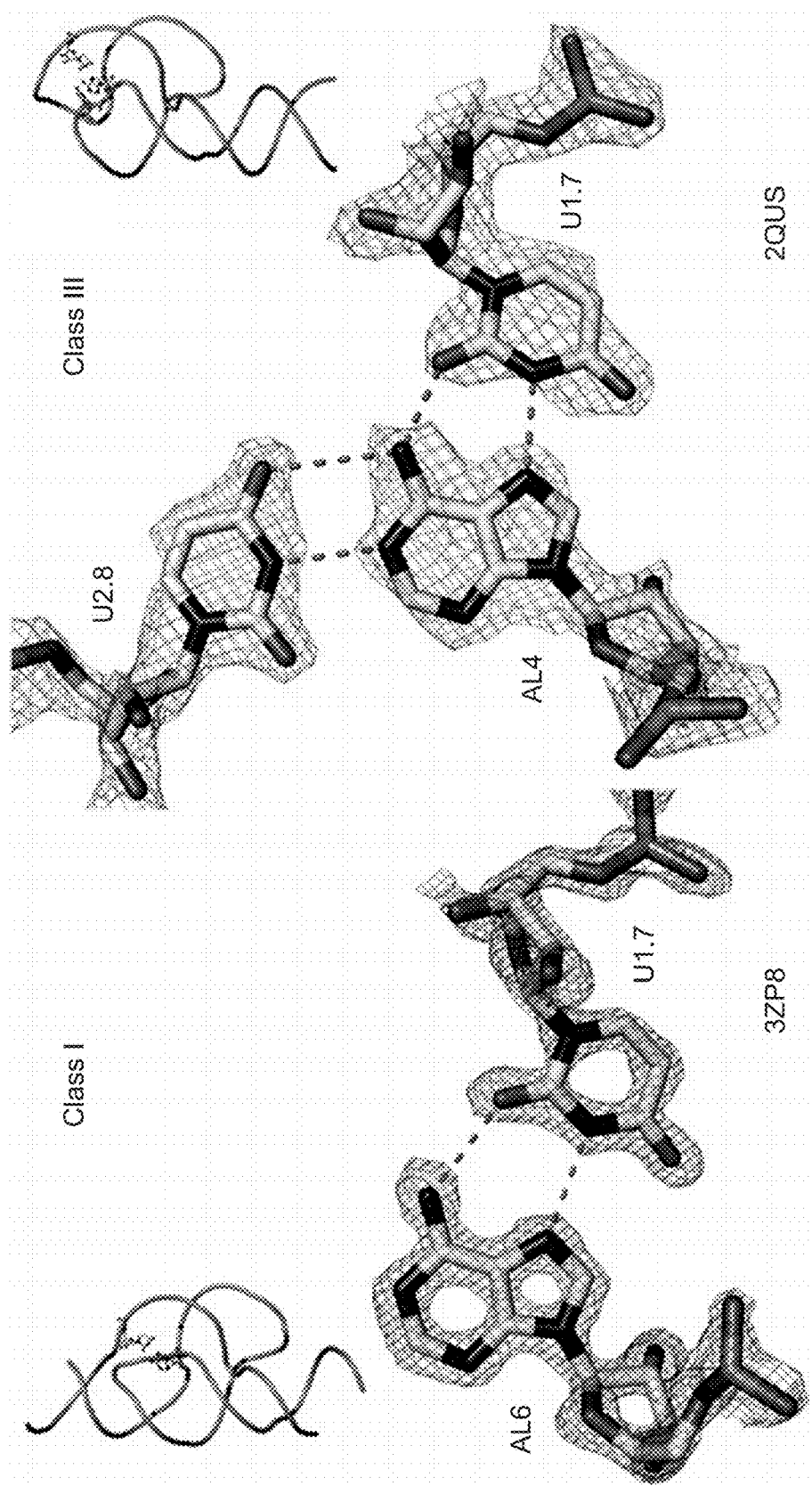
FIG. 5 shows crystal structures of full-length Class I and Class III hammerhead ribozymes. A Class I hammerhead ribozyme structure (3ZP8), shown on the left side of the figure, was obtained at 1.55 Å resolution, enabling the location of all non-hydrogen atoms to be clearly defined. The ribbon structure in the top left depicts the backbone fold in which a conserved trans-Hoogsteen AU pair within the tertiary contact region between Stem-loop II and Stem I is highlighted. A close-up of the trans-Hoogsteen AU pair, conserved in the Smα1 and mammalian 3'-UTR hammerheads, is shown in the context of a defining 2Fo-Fc electron density map (indicated as a mesh) contoured at 2.0 r.m.s.d. A Class III hammerhead ribozyme structure (2QUS), shown on the right side of the figure, was obtained at 2.4 Å resolution. The ribbon structure in the top right depicts the backbone fold in which a conserved trans-Hoogsteen AU pair within the tertiary contact region between Stem-loop II and Stem-loop I is highlighted, and an additional U (2.8) participating in a Watson-Crick pairing interaction with the A, shown in white, forms a base triple. A close-up of the base triple that includes the trans-Hoogsteen AU pair, conserved in many Class III hammerheads as described in the text, is shown in the context of a defining 2Fo-Fc electron density map (indicated as a mesh) at 1.8 r.m.s.d. The conserved trans-Hoogsteen AU pair is the only structural feature the Class I and Class III hammerhead tertiary contacts share in common.

The minimal hammerhead ribozyme construct consists of a conserved core of mostly invariant residues (FIG. 3, Panel A). Optimized minimal hammerhead ribozymes typically cleave with a turnover rate of about 1 per minute under standard single-turnover conditions (10 mM $Mg^{2+}$, pH 7.5). In contrast, catalytically uncompromised full-length hammerhead ribozymes (FIG. 3, Panel B) derived from natural sequences that include an array of tertiary contacts between loops in Stems I and II may experience up to a 100-fold rate enhancement compared to corresponding minimal hammerhead sequences. X-ray crystal structures of two different full-length natural hammerheads (FIG. 5) reveal two very different sets of these tertiary interactions. Despite the differences, both sets of tertiary contacts have the same net effect of stabilizing the active site structure in the conformation required for catalysis, with the general base (G12) poised to abstract the 2'-proton of C17 to activate the nucleophile positioned for in-line attack.

Unlike the mostly invariant sequence of the minimal hammerhead RNA catalytic core, there is little apparent sequence conservation within the tertiary contact regions of the more catalytically active full-length hammerhead RNAs. For this reason, the existence of the tertiary contact remained undetected until 16 years after the discovery of the hammerhead ribozyme. The complexity and idiosyncratic nature of the tertiary contact interactions have impeded development of synthetic intermolecular highly active full-length hammerhead ribozyme/target systems with non-natural sequences for biochemical investigations and nucleolytic reagents. The hammerhead RNA derived from satellite tobacco ringspot virus (sTRSV) is a typical example. The crystal structure (2QUS) reveals an extensive network of tertiary contacts between the GUGA tetraloop capping Stem II and an irregular loop capping Stem I (FIG. 3, Panel B), which has previously defied separation into discrete catalytic and target strands. For example, the trans-Hoogsteen pair between AL4 and U1.7 in fact is part of a base triple that also involves Watson-Crick pairing between AL4 and U2.8 (FIG. 3, Panel B, upper inset).

It was found that as long as the Hoogsteen pair between U1.7 and AL4 is maintained, all of the other tertiary contacts between Stems I and II, including the participation of U2.8 in the base triple, can be eliminated without compromising the enhanced catalytic activity of the ribozyme. If a minimal hammerhead catalytic strand is constructed with a 5' end beginning exactly at position 2.6 (FIG. 3, Panel A), a target with U1.7 will be free to pair with AL4 without interference or competition, as shown in FIG. 3, Panel B. Minimal intermolecular hammerhead ribozymes possessing the natural sTRSV Stem-loop II sequence that begin at position 2.6 ($HH_{min-AL4:U1.7}$) have essentially the same enhanced catalytic activity (FIG. 4 and Table 1) previously observed only in optimized full-length sTRSV-derived hammerhead constructs ($HH_{16-T2}$), and significantly greater activity than the corresponding non-optimized sequences ($HH_{16-T1}$).

TABLE 1

Single turnover kinetics for sTRSV-like hammerhead ribozymes: Integrated rate equation curve-fitting parameters

| HH construct | $k_{obs}$ @ pH 5.6 (min) | $k_{obs}$ @ pH 6 (min) | $k_{obs}$ @ pH7.5 (min) | Fraction cleaved $F_o$ | $F_{sat}$ | RNA sequences assayed (5' to 3') |
|---|---|---|---|---|---|---|
| $HH_{min-AlA:U1.7}$ | 0.77 ± 0.11 | 1.9 ± 0.3 $^a$ | 61. ± 9. $^a$ | 0.11 | 0.9 | GACUGUCUGAUGAGU CCGUGAGGACGAAAC CCA (SEQ ID NO: 1) |
| $HH_{min-WC-AU}$ | 0.02 ± 0.01 $^a$ | 0.05 ± 0.01 $^a$ | 1.5 ± 0.2 | 0.15 | 0.69 | GGCCCAUAAUAGACU GUCUGAUGAGUCCGU GAGGACGAAACCCA (SEQ ID NO: 3) |
| $HH_{min-5'GUU}$ | 0.19 ± 0.03 | 0.48 ± 0.07 $^a$ | 15. ± 2 $^a$ | 0.14 | 0.88 | GUUGACUGUCUGAUG AGUCCGUGAGGACGA AACCCA (SEQ ID NO: 4) |
| $HH_{min-GL3A}$ | 0.063 ± 0.02 | 0.15 ± 0.05 $^a$ | 5.0 ± 1.6 $^a$ | 0.07 | 0.5 | GACUGUCUGAUGAGU CCGUAAGGACGAAAC CCA (SEQ ID NO: 5) |
| $HH_{min-GL3U}$ | 1.2 ± 0.2 | 3.0 ± 0.6 $^a$ | 95. ± 20 $^a$ | 0.11 | 0.53 | GACUGUCUGAUGAGU CCGUUAGGACGAAAC CCA (SEQ ID NO: 6) |

TABLE 1-continued

Single turnover kinetics for sTRSV-like hammerhead ribozymes:
Integrated rate equation curve-fitting parameters

| HH construct | $k_{obs}$ @ pH 5.6 (min) | $k_{obs}$ @ pH 6 (min) | $k_{obs}$ @ pH7.5 (min) | Fraction cleaved $F_o$ | Fraction cleaved $F_{sat}$ | RNA sequences assayed (5' to 3') |
|---|---|---|---|---|---|---|
| $HH_{min-GL3A-5'GUU}$ | 1.0 ± 0.2 | 2.5 ± 0.6 [a] | 79. ± 20 [a] | 0.05 | 0.76 | GUUGACUGUCUGAUG AGUCCGUAAGGACGA AACCCA (SEQ ID NO: 7) |
| $HH_{min-GL3U-5'GUU}$ | 1.2 ± 0.2 | 3.0 ± 0.6 [a] | 95. ± 20 [a] | 0.1 | 0.68 | GUUGACUGUCUGAUG AGUCCGUUAGGACGA AACCCA (SEQ ID NO: 8) |
| $HH_{min-AL4C:U1.7}$ | 0.39 ± 0.03 | 0.96 ± 0.07 [a] | 31. ± 2 [a] | 0.04 | 0.4 | GACUGUCUGAUGAGU CCGUGCGGACGAAAC CCA (SEQ ID NO: 9) |
| $HH_{3zp8-min-AL4:U1.7}$ | 0.30 ± 0.05 | 0.74 ± 0.12 [a] | 24. ± 4 [a] | 0.03 | 0.55 | UACCAGCUGAUGAGU CCCAAAU AGGACGAA ACGCC (SEQ ID NO: 10) |
| $HH_{substrate}{}^1$ | | | | | | Cye3_ UGGGGUCACAGUCUAU UAUGGGG (SEQ ID NO: 11) |
| $HH_{substrate}{}^8$ | | | | | | Cye3_ GGCGUCCUGGUAUCC AAUCC (SEQ ID NO: 12) |
| $HH_{16-T1}{}^{19}$ | 0.25 [a] | 0.62 [b] | 20. [a] | | | (Previously published |
| $HH_{16-T2}{}^{19}$ | 0.76 [a] | 1.9 [b] | 60. [a] | | | values[19] are provided |
| $HH_{16-min}{}^{19}$ | 0.01 [a] | 0.03 [a,b] | 1. [c] | | | as external controls) |

\* Nelson et al. (2005) *Biochemistry* 44:14577-14585.
[a] Extrapolated rate constant, using $k_{obs(extrapolated)} = k_{obs} \times 10^{\Delta pH}$.
[b] $k_{obs}$ values calculated using $k_{obs} = (k_{+2} + k_{-2})$, where $k_{±2}$ are reported rate constants.
[c] Observed reported rate constant.

To demonstrate that the AU Hoogsteen pair is responsible for the observed catalytic enhancement relative to the typical minimal hammerhead, an otherwise identical hammerhead catalytic strand was designed to form eight additional canonical Watson-Crick base pairs (designated $HH_{min-WC-AU}$ in Table 1) with U1.7 through G1.15 of the target in Table 1, thus preventing formation of the Hoogsteen pair. This minimal hammerhead extends the Stem I A-form helix, (FIG. 3, Panel B, lower inset), preventing AL4 from participation in a trans-Hoogsteen interaction with U1.7. This construct serves as an important negative control, as it displays typical minimal hammerhead ribozyme kinetics (compare to $HH_{16-min}$ in Table 1).

To test the hypothesis that all of the interactions apart from the trans-Hoogsteen AU pair exist primarily to prevent deleterious alternative paring interactions from taking place that potentially interfere with the trans-Hoogsteen pair formation, a hammerhead (designated $HH_{min-5'GUU}$ in Table 1) having the same sequence as $HH_{min-AL4:U1.7}$, but with an additional GUU sequence appended to the 5' end was constructed. These three additional nucleotides appear to interfere with formation of the required Hoogsteen pair to some extent, as its rate is decreased four-fold. However, changing the third nucleotide in the Stem-Loop II tetraloop from G to A (designated $HH_{min-GL3A-5'GUU}$ in Table 1) or G to U (designated $HH_{min-GL3U-5'GUU}$ in Table 1) rescues the ribozyme with the 5'GUU sequence. Based upon the crystal structure of the active, full-length hammerhead, the 5'G is predicted to form a single hydrogen bond with GL3 in $HH_{min-5'GUU}$, which is likely not enough to prevent formation of an alternative, inhibitory conformation that may (imperfectly) extend Stem I, preventing formation of the Hoogsteen pair. Substituting the G at the L3 position with an A potentially provides a second hydrogen bond between the Hoogsteen faces of both purines, which apparently restores $k_{+2}$ as well as enhancing $k_{-2}$, so that the overall $k_{obs}$ increases from 0.77 min$^{-1}$ to 1.0 min$^{-1}$, and the fraction cleaved as equilibrium is approached decreases from 0.9 to 0.76. When G at position L3 is instead replaced with a U, a GU wobble pair can potentially form, which similarly restores $k_{+2}$ as well as enhancing $k_{-2}$, this time with the fraction cleaved decreasing to 0.68, similar to $HH_{min-WC-AU}$, in which Stem I is extended at the expense of formation of the required tertiary interaction. A hammerhead (designated $HH_{min-GL3A}$ in Table 1) having the same sequence as $HH_{min-AL4:U1.7}$, but with the G in the third position of the tetraloop capping Stem II replaced with an A, displayed only marginally more activity that the control minimal hammerhead $HH_{min-WC-AU}$. This may suggest that AL3 deleteriously competes with AL4 for pairing with U1.7. Another hammerhead (designated $HH_{min-GL3U}$ in Table 1) having the same sequence as $HH_{min-GL3A}$, but with GL3A replaced with GL3U, is at least as active as $HH_{min-AL4:U1.7}$, which may suggest that UL3 cannot compete with AL4 for pairing with U1.7.

Figure 6:
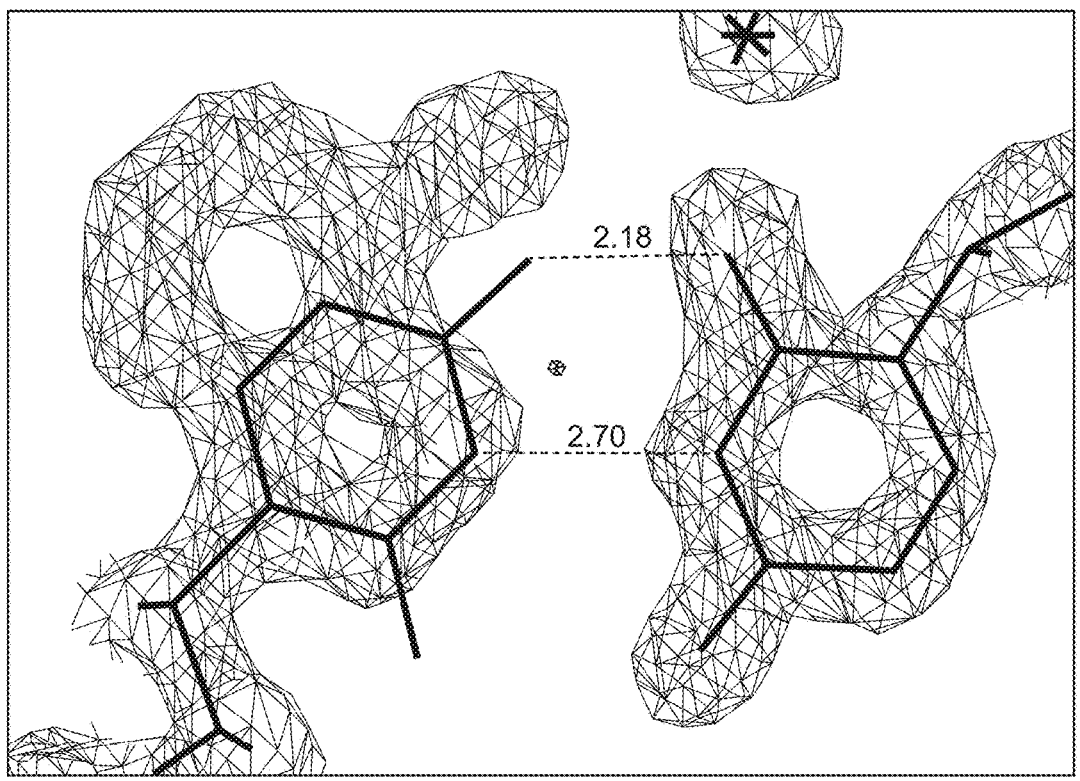
FIG. 6 shows in silico modeling of the AL4C mutation using COOT (Emsley et al., 2010. *Acta Crystallogr*. D(66): 486-501). The 1.55 Å resolution electron density corresponds to the observed AL4-U1.7 trans-Hoogsteen base pair observed in 3ZP8. The A was simply changed to a C, while retaining the N1 position of the nucleotide base as well as the ribose and phosphate positions. A 180° manual rotation about the glycosylic bond was performed to transform the nucleotide from the anti-conformation to the syn-conformation. No positional refinement or optimizations were performed. The result illustrated here demonstrates that the AL4C mutation is an isostructural substitution that preserves the conformation and hydrogen bonding pattern observed in the trans-Hoogsteen AU base pair.
Figure 7A:
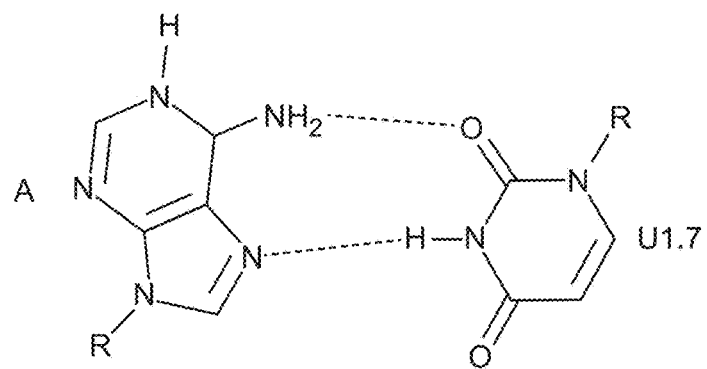
FIG. 7 shows base-pairing between a nucleotide of the stem II loop (left) of the catalytic strands of a minimal hammerhead ribozyme of the present disclosure and a nucleotide at position 1.7 of the target strand (right).
Figure 7B:
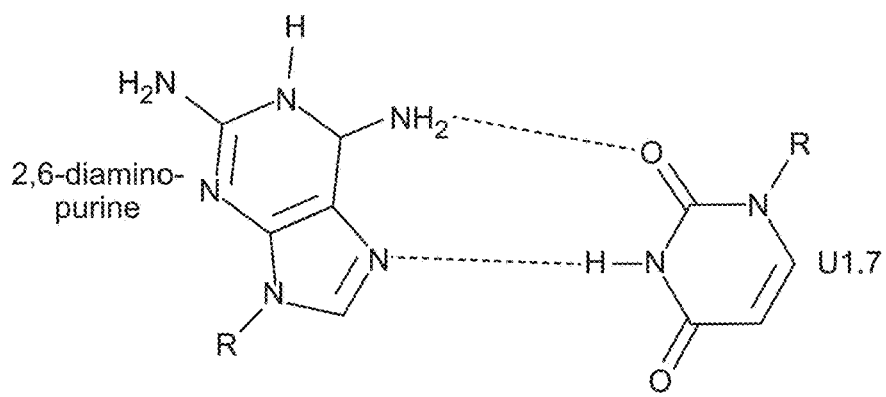
Figure 7C:
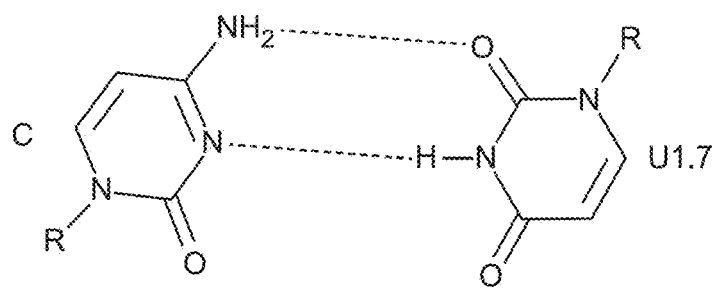
Figure 7D:
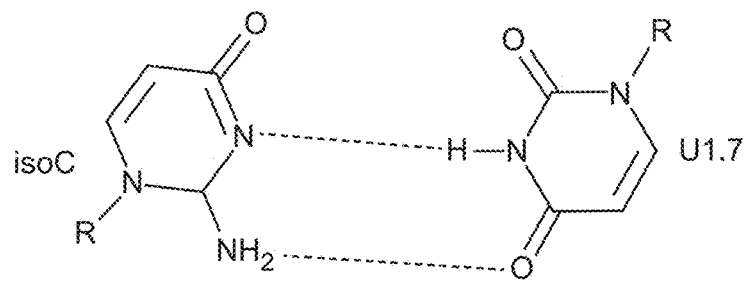

When AL4 was replaced with a C in the sequence of $HH_{min-AL4:U1.7}$ (designated $HH_{min-AL4C:U1.7}$ in Table 1), the CL4 adopted the syn-conformation, a parallel CU base-pairing interaction, isostructural with respect to an AU trans-Hoogsteen base pair, which is maintained without requiring perturbation of the positions of either ribose moiety or the adjacent phosphates. This control, which is only twofold less active than the sequence in $HH_{min-AL4:U1.7}$, is consistent with the trans-Hoogsteen AU pairing interaction observed in the Class I and Class III hammerhead crystal structures and is inconsistent with possible aberrant alternative pairing interactions between AL4 and U1.7, such as reverse Watson-Crick pairing. $HH_{min-AL4C:U1.7}$ represents a comparatively drastic AL4C mutation which preserves much of the catalytic enhancement and experimentally corroborates the assumption that the conserved trans-Hoogsteen AL4-U1.7 interaction observed in the Class I and Class III full-length hammerhead crystal structures is present in the minimal hammerhead construct with enhanced activity. CL4 in the syn-conformation enables formation of a parallel CU pair, in which the hydrogen bond donor and acceptor of CL4 are isosteric with those on the Hoogsteen face of AL4, consistent with the conserved trans-Hoogsteen AL4-U1.7 interaction (FIG. 6) and inconsistent with other potential base-pairing interactions.

These results indicate that the AL4-U1.7 trans-Hoogsteen base-pair alone is responsible for increasing $k_{+2}$ by over a factor of ~50, and that the increases in the ligation rate, $k_{-2}$, as observed in the experimental controls, may be due to the increase in hydrogen bonding base-pairing contacts, whether they occur within the tertiary contact region of full-length hammerheads, or simply as a result of extending Stem I in the case of minimal hammerheads.

Conclusion

This study unambiguously demonstrates that the AL4-U1.7 trans-Hoogsteen base-pair is both necessary and sufficient to confer the >50-fold enhanced cleavage activity ($k_{+2}$) characteristic of full-length hammerhead ribozymes possessing extensive tertiary interactions. The remaining tertiary interactions, which do not appear to adhere to any obvious sequence conservation patters, therefore most likely exist primarily to prevent deleterious alternative structures from forming that are incompatible with formation of the required trans-Hoogsteen pair, but can also enhance the reverse reaction (albeit in a non-sequence-specific manner). If a minimal intermolecular hammerhead ribozyme is designed as an RNA cleavage reagent with this in mind, no need for designing the additional tertiary contacts ever arises. The design problem instead reduces quite simply and rationally to that of targeting target strands restricted to having a U at position 1.7. The fully-active minimal catalytic strand can then be designed with a 5'-end exactly at position 2.6, and in such a way as to preserve the natural sTRSV hammerhead stem-loop II GUGA sequence. In addition, the observation that some RNA tertiary structural interactions may function primarily to prevent deleterious alternative structural interactions from forming is likely generalizable to other structured RNAs.

A single additional base-pairing interaction in the minimal hammerhead ribozyme transforms an RNA sequence possessing typically modest catalytic activity into one possessing greatly enhanced catalytic activity that is instead typical of full-length natural hammerhead RNAs that have additional extensive tertiary contact interactions. Formation of this additional base-pairing interaction requires only that the target RNA sequence contains a U at a position seven nucleotides 3' to the cleavage site. No additions or changes are required in the minimal hammerhead ribozyme catalytic strand sequence, (providing the naturally-occurring GNRA tetraloop of Stem II is maintained). This finding demonstrates that a single Hoogsteen base-pairing interaction is both necessary and sufficient for stabilizing the ribozyme active site, including alignment of the attacking nucleophile for the required SN2 hammerhead ribozyme reaction mechanism. This finding also implies that the idiosyncratic arrays of additional tertiary contacts observed in all naturally-occurring full-length hammerhead sequences have evolved piecemeal to prevent deleterious alternative pairing interactions within the context of the variety of natural sequences arising in vivo. Finally, this finding greatly simplifies and rationalizes the design of fast-cleaving engineered synthetic ribozymes as RNA nucleolytic reagents and as subjects for kinetic and mechanistic investigations.

Materials and Methods

RNA Preparation and Purification

The hammerhead RNA catalytic strands used in this study were prepared using T7 RNA polymerase runoff transcription. The target RNA used in this study was obtained as a commercially prepared synthesis.

DNA templates for transcription were obtained as follows: 2 nM each of partially overlapping complementary DNA oligomers (IDT Coralville, Iowa) designed to incorporate a 5' T7 promotor binding sequence and hammerhead RNA, were annealed and extended using 10 U/µl MMLV reverse transcriptase (Life Technologies, Carlsbad, Calif.) in a mixture containing 0.5 mM each dNTP, 3 mM MgCl2, 75 mM KCl, 10 mM dithiothreitol (DTT), and 50 mM Tris-HCl (pH 8.3), which was incubated at 42° C. for 1 hr.

The RNAs were transcribed and purified as follows: The extended products created using the above procedure were transcribed using 15 U/µl T7 RNA polymerase, 0.001 U/µl inorganic pyro-phosphatase (NEB, Ipswich, Mass.), 5 mM each NTP (NEB), 25 mM MgCl2, 2 mM spermidine, 10 mM DTT, and 40 mM Tris-HCl (pH 7.9), which was incubated at 37° C. for 2 hr. Then, 0.5 U/µl DNase I (Roche Applied Science, Pleasanton Calif.) was added, and the mixture was incubated at 37° C. for an additional 30 minutes. Transcribed RNA was purified on a 15% denaturing PAGE gel. RNA eluted from the gel was purified by ethanol precipitation, and resuspended at a concentration of 100 µM in water.

Activity Assays

Single turnover cleavage assays were performed using conditions similar to those described in Canny et al. (2004) J. Am. Chem. Soc. 126:10848-10849, except that the ribozyme catalytic strand was in >50-fold excess to the synthetic Cye3 5'-labeled target strand (IDT), with a catalytic concentration of 20 µM. Assay conditions for the fast-cleaving constructs were performed (as has been done previously) at lower pH, i.e., 50 mM MES pH 5.6, 100 mM NaCl, 0.1 mM EDTA, and 10 mM MgCl$_2$ at 27° C., or under standard higher-pH reaction conditions for minimal hammerheads, i.e., 50 mM Tris-HCl pH 7.4, 100 mM NaCl, 0.1 mM EDTA, and 10 mM MgCl$_2$ at 27° C., for the slower-cleaving ribozymes. Prior to adding MgCl$_2$, the catalytic and target strands were heated to 95° C. for 2 min, then 65° C. for 2 min, then allowed to equilibrate at 27° C. for 5 min. At this point, a sample was removed and designated as the zero time point. The reaction was initiated by adding MgCl$_2$, and the subsequent triplicate time points (at 15 seconds, 30 seconds, 45 seconds, 1 minute, 2 minutes, 3 minutes, 5 minutes, 15 minutes, 30 minutes, and 60 minutes) samples were collected and flash frozen in gel loading buffer (47.5% formamide, 10 mM EDTA, 0.01% SDS, 0.01% bromophenol blue) immersed in liquid nitrogen. During our initial characterization experiments, additional time points ranging to several hours were obtained, but these did not indicate any further increases in the cleavage fraction, and the dye label appears to deteriorate.

Cleavage products were separated on a 20% denaturing PAGE gel, and quantified on a Typhoon Trio phosphorimager (GE Healthcare UK) using Image Jay (Rasband, W. S., ImageJ, U. S. National Institutes of Health, Bethesda, Md., USA, 1997-2014.)

Figure 4:
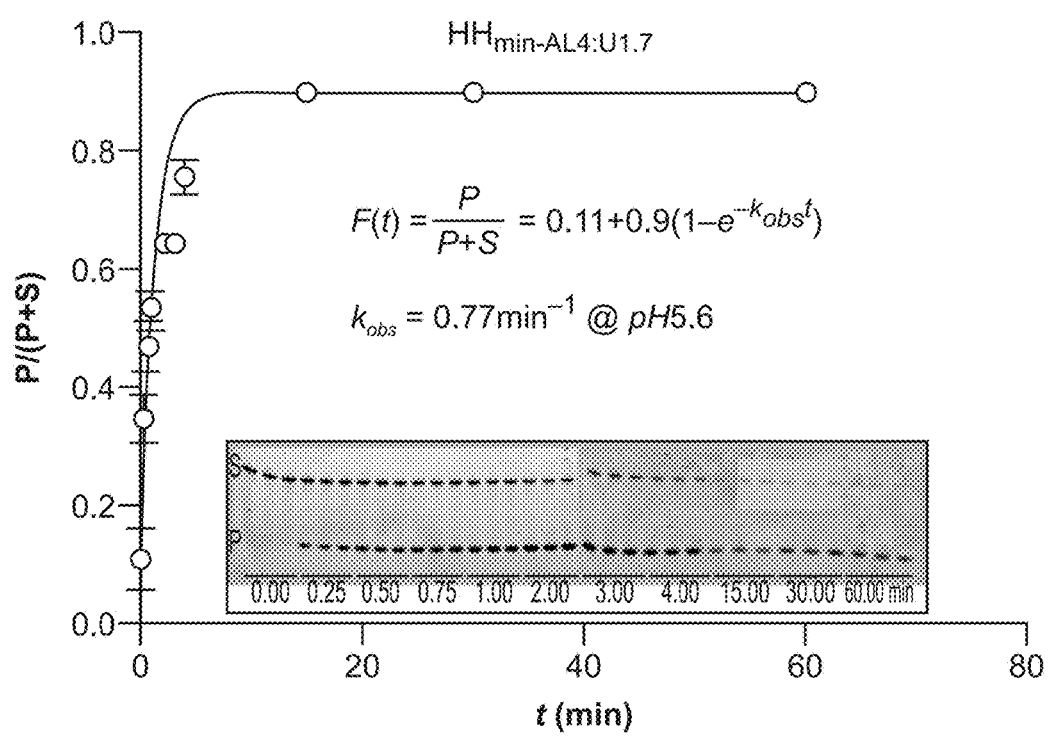
FIG. 4 shows representative single-turnover kinetic data for the catalytic strand of the minimal ribozyme shown in FIG. 3 and summarized in the first row of Table 1. The fraction of product produced as a function of time, F(t), was quantified in triplicate by polyacrylamide gel electrophoresis separation of fluorescently-labelled target and product (inset). The data were fit to a standard exponential function, where Fo=0.11 is the initial fraction of cleavage product, and Fsat=0.9 is the estimated extent of cleavage based upon the final three time points. Non-linear regression analysis was performed to estimate kobs, as described in the Experimental section. The most conservative estimate for kobs is 0.77/min at pH 5.6, which is essentially the same as kobs for an optimized one-stranded full-length hammerhead based on the sTRSV natural full-length hammerhead RNA sequence (HH16-T2), as shown in Table 1.

Triplicate data were then fitted to a standard three-parameter exponential rise function in GraphPad Prism6 (San Diego, Calif.) using robust nonlinear regression as shown in FIG. 4.

$$F(t)=F_o+F_{sat}(1-e^{-k_{obs}t}) \quad \text{Formula I}$$

The first parameter, the fraction of cleavage at t=0, Fo, was constrained to be less than or equal to the average initial fraction cleaved observed in each dataset, and the second parameter, Fsat, (saturation, or estimated extent of cleavage), was constrained to be greater than or equal to the average value of the greatest extent of cleavage observed in the dataset. The third parameter, kobs, was then obtained via nonlinear regression analysis implemented within Prism6. It was observed that adhering to this procedure yielded the most consistent and conservative estimates of kobs, and enabled comparison with the previously published results given in the last three rows of Table 1.

Example 2

Minimal Hammerhead Ribozyme Sequence Derived from the Smα1-Like 3ZP8-Crystallized Hammerhead Sequence A minimal hammerhead ribozyme sequence derived from the Smα1-like 3ZP8-crystallized hammerhead sequence (designated $HH_{3ZP8-min-AL4:U1.7}$ in Table 1) maintains the crystallographically observed AL6-U1.7 trans-Hoogsteen base pair. The 5'-end of the enzyme strand terminates at position 2.6. This hammerhead sequence is 2.5-fold less active than the $HH_{min-AL4:U1.7}$ sequence assayed and about two fold less active than the originally crystallized 3ZP8 sequence. This control demonstrates that the experimental observations relating to the sTRSV+-like Class III ribozymes are generalizable to the Class I hammerheads as well. The only remaining substantive difference between this minimized sequence and that of $HH_{min-AL4:U1.7}$ is the six-nucleotide Stem-loop II versus the four-nucleotide Stem-loop II of the sTRSV+-like ribozymes.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A catalytic strand of a minimal hammerhead ribozyme, comprising:
   a catalytic core region comprising the sequence CUGANGA, wherein N is any nucleotide or a non-nucleotide spacer linkage;
   a stem I-forming region;
   a stem II region comprising helical strands;
   a stem II loop that connects the helical strands of the stem II region, wherein the stem II loop comprises an adenine, a cytosine, or a natural or non-natural nucleotide base having hydrogen bond donor and acceptor functionalities at positions analogous to those of adenine or cytosine; and
   a stem III-forming region,
   wherein the catalytic strand hybridizes to a target strand via the stem I-forming region and the stem III-forming region, wherein the stem I-forming region forms exactly 6 base pairs with the target strand, wherein the adenine, cytosine, or natural or non-natural nucleotide base of the stem II loop base-pairs with a uracil or cytosine at position 1.7 of the target strand, and wherein the 5' nucleotide of the stem I-forming region base pairs with the nucleotide at position 1.6 of the target strand.

2. The catalytic strand of claim 1, wherein the stem I-forming region base pairs with 6 contiguous nucleotides of the target strand.

3. The catalytic strand of claim 1, wherein the stem II loop is a GNRX tetraloop, wherein:
   G is a guanine;
   N is any nucleotide;
   R is a purine; and
   X is adenine, cytosine, or a natural or non-natural nucleotide base having hydrogen bond donor and acceptor functionalities at positions analogous to those of adenine or cytosine.

4. The catalytic strand of claim 3, wherein R is guanine or adenine.

5. The catalytic strand of claim 1, wherein the target strand is an RNA strand.

6. The catalytic strand of claim 5, wherein the RNA is transcribed from a tumor-specific gene or a tumor-associated gene.

7. The catalytic strand of claim 5, wherein the RNA is from a pathogen.

8. The catalytic strand of claim 7, wherein the pathogen is Human Immunodeficiency Virus (HIV).

9. The catalytic strand of claim 8, wherein the target strand is an RNA transcribed from an HIV envelope protein gene.

10. The catalytic strand of claim 9, wherein the catalytic strand comprises the nucleotide sequence:

(SEQ ID NO: 1)
5'-GACUGUCUGAUGAGUCCGUGAGGACGAAACCCA-3'.

11. The catalytic strand of claim 10, wherein the target strand comprises the nucleotide sequence:

(SEQ ID NO: 2)
5'-UGGGUCACAGUCUAUUAUGGG-3'.

12. A pharmaceutical composition comprising:
catalytic strand of a minimal hammerhead ribozyme of claim 1; and
a pharmaceutically-acceptable excipient.

13. A cell comprising:
catalytic strand of a minimal hammerhead ribozyme of claim 1, wherein the cell is present in a cell culture medium.

14. A nucleic acid that encodes a catalytic strand of a minimal hammerhead ribozyme of claim 1.

15. An expression vector comprising the nucleic acid of claim 14.

16. A population of minimal hammerhead ribozyme catalytic strands, comprising:
two or more subpopulations of distinct minimal hammerhead ribozyme catalytic strands, wherein the catalytic strands of the two or more subpopulations comprise:
a catalytic core region comprising the sequence CUGANGA, wherein N is any nucleotide or a non-nucleotide spacer linkage;
a stem I-forming region;
a stem II region comprising helical strands;
a stem II loop that connects the helical strands of the stem II region, wherein the stem II loop comprises an adenine, cytosine, or a natural or non-natural nucleotide base having hydrogen bond donor and acceptor functionalities at positions analogous to those of adenine or cytosine; and
a stem III-forming region,
wherein the catalytic strand hybridizes to a target strand via the stem I-forming region and the stem III-forming region, wherein the stem I-forming region forms exactly 6 base pairs with the target strand, wherein the adenine, cytosine, or natural or non-natural nucleotide base of the stem II loop base pairs with a uracil or cytosine at position 1.7 of the target strand, and wherein the 5' nucleotide of the stem I-forming region base pairs with the nucleotide at position 1.6 of the target strand.

17. A method of cleaving a target nucleic acid strand, comprising:
contacting a target nucleic acid strand with the catalytic strand of a minimal hammerhead ribozyme of claim 1 under conditions in which the catalytic strand cleaves the target nucleic acid strand.

18. A method comprising:
administering to a subject in need thereof a therapeutically effective amount of a catalytic strand of a minimal hammerhead ribozyme of claim 1.

19. A method of treating Human Immunodeficiency Virus (HIV) infection in a subject, comprising:
administering to a subject infected with HIV a catalytic strand of a minimal hammerhead ribozyme of claim 8, to treat the HIV infection in the subject.

20. A kit comprising:
catalytic strand of a minimal hammerhead ribozyme of claim 1; and
instructions for using the catalytic strand to cleave a target nucleic acid strand, or
a therapeutically effective amount of a catalytic strand of a minimal hammerhead ribozyme of claim 1; and
instructions for administering the catalytic strand to a subject in need thereof.

* * * * *